US012288601B2

(12) United States Patent
Tatsutani et al.

(10) Patent No.: US 12,288,601 B2
(45) Date of Patent: Apr. 29, 2025

(54) FLOW CYTOMETER, DATA TRANSMISSION METHOD, AND INFORMATION PROCESSING SYSTEM

(71) Applicant: SYSMEX CORPORATION, Kobe (JP)

(72) Inventors: Hiroo Tatsutani, Kobe (JP); Tomohiro Tsuji, Kobe (JP); Hajimu Kawakami, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 527 days.

(21) Appl. No.: 16/579,952

(22) Filed: Sep. 24, 2019

(65) Prior Publication Data

US 2020/0098452 A1 Mar. 26, 2020

(30) Foreign Application Priority Data

Sep. 26, 2018 (JP) .................... 2018-179994

(51) Int. Cl.
*G16H 10/20* (2018.01)
*G01N 15/1429* (2024.01)
(Continued)

(52) U.S. Cl.
CPC .......... *G16H 10/20* (2018.01); *G01N 15/1429* (2013.01); *G16H 10/40* (2018.01); *G16H 10/60* (2018.01)

(58) Field of Classification Search
CPC ........ G16H 10/20; G16H 10/40; G16H 10/60; G01N 35/00871; G01N 15/14;
(Continued)

(56) References Cited

U.S. PATENT DOCUMENTS 8,731,844 B2 * 5/2014 Herzenberg ....... G01N 15/1429
702/22
9,934,364 B1 * 4/2018 Kumar .................. G06N 3/045
(Continued)

FOREIGN PATENT DOCUMENTS

CN 101315323 A 12/2008
CN 101620223 A 1/2010
(Continued)

OTHER PUBLICATIONS

"Coordination between flow cytometry and LIS (hospital information system)", URL: https://www.bc-cytometry.com/FCM/FCM/fcm_08.html, Retrieved in Sep. 2019, Cited in the Specification.
(Continued)

*Primary Examiner* — Yoshihisa Ishizuka
(74) *Attorney, Agent, or Firm* — METROLEX IP LAW GROUP, PLLC; Robert L. Scott, Esq.

(57) ABSTRACT

A flow cytometer according to one or more aspects may include: a particle data acquisition unit that measures particles in a sample to acquire particle data including optical information of the particles; and a transmission unit that transmits at least one of the particle data and data on a particle distribution diagram of the particles, generated based on the particle data, to at least one of a hospital information system that supports hospital operations and a clinical laboratory information system that supports clinical test operations.

17 Claims, 14 Drawing Sheets

(51) Int. Cl.
*G16H 10/40* (2018.01)
*G16H 10/60* (2018.01)

(58) Field of Classification Search
CPC .......... G01N 15/1429; G01N 15/1436; G01N 2035/00841; G01N 2035/00831
See application file for complete search history.

(56) References Cited

U.S. PATENT DOCUMENTS

| | | | |
|---|---|---|---|
| 2003/0235919 A1* | 12/2003 | Chandler | G01N 15/1456 436/63 |
| 2007/0282629 A1* | 12/2007 | Plambeck | G16H 10/60 600/300 |
| 2009/0164253 A1 | 6/2009 | Lyshkow | |
| 2012/0309636 A1* | 12/2012 | Gibbons | C12Q 1/42 435/6.12 |
| 2013/0102087 A1* | 4/2013 | Kasdan | G01N 33/5094 436/172 |
| 2014/0092094 A1 | 4/2014 | Itoh et al. | |
| 2014/0092118 A1 | 4/2014 | Itoh et al. | |
| 2014/0136233 A1 | 5/2014 | Atkinson et al. | |
| 2014/0193892 A1* | 7/2014 | Mohan | G01N 15/1434 435/287.2 |
| 2015/0269325 A1 | 9/2015 | Ohta et al. | |
| 2016/0169786 A1* | 6/2016 | Albitar | G06F 18/24323 702/19 |
| 2016/0320420 A1* | 11/2016 | Yundt-Pacheco | G16Z 99/00 |
| 2017/0176425 A1* | 6/2017 | Shehada | G01N 35/00693 |
| 2017/0315110 A1* | 11/2017 | Chou | G01N 33/48792 |
| 2017/0322138 A1 | 11/2017 | Wolf et al. | |
| 2018/0003634 A1 | 1/2018 | Bo et al. | |
| 2018/0025117 A1 | 1/2018 | Kanada | |

FOREIGN PATENT DOCUMENTS

| | | | | |
|---|---|---|---|---|
| CN | 102472743 | A | 5/2012 | |
| CN | 105164508 | A | 12/2015 | |
| CN | 106687810 | A | 5/2017 | |
| CN | 107389536 | A | 11/2017 | |
| EP | 2202506 | A2 | 6/2010 | |
| EP | 2202506 | A3 | 10/2017 | |
| JP | H08178826 | A | 7/1996 | |
| JP | H1090163 | A | 4/1998 | |
| JP | 2004522204 | A | 2/2003 | |
| JP | 2003106984 | A | 4/2003 | |
| JP | 2003-162580 | A | 6/2003 | |
| JP | 2005287927 | A | 10/2005 | |
| JP | 2009092678 | A | 4/2009 | |
| JP | 2010-097476 | A | 4/2010 | |
| JP | 2010216868 | A | 9/2010 | |
| JP | 2011064537 | A | 3/2011 | |
| JP | 2012-038349 | A | 2/2012 | |
| JP | 2014-067321 | A | 4/2014 | |
| JP | 2014-071693 | A | 4/2014 | |
| JP | 2014-071694 | A | 4/2014 | |
| JP | 2014062760 | A | 4/2014 | |
| JP | 2014062917 | A | 4/2014 | |
| JP | 2014-109835 | A | 6/2014 | |
| JP | 2016-184221 | A | 10/2016 | |
| JP | 2018505392 | A | 2/2018 | |
| JP | 2018124171 | A | 8/2018 | |
| JP | 2018179994 | A | 11/2018 | |
| JP | 2023029386 | A | 12/2022 | |
| WO | WO-0108081 | A1 * | 2/2001 | ......... G01N 15/1475 |
| WO | WO-2007050877 | A2 * | 5/2007 | .......... G06F 19/321 |
| WO | 2007050877 | A3 | 11/2007 | |
| WO | 2009/002322 | A1 | 12/2008 | |
| WO | 2010052849 | A1 | 5/2010 | |
| WO | 2011011101 | A | 1/2011 | |
| WO | 2014/127285 | A1 | 8/2014 | |

OTHER PUBLICATIONS

"ALCS ver 1.0", URL: http://finggal-link.com/lis/alcs.html, Retrieved in Sep. 2019, Finggal Link Co., Ltd.
The extended European search report ("EESR") issued on Feb. 19, 2020 in a counterpart European patent application.
The Communication pursuant to Article 94(3) EPC issued on Mar. 30, 2022, in a counterpart European patent application.
Japanese Office Action mailed on Jun. 2, 2022 in a counterpart Japanese patent application.
The Communication Pursuant to Article 94(3) EPC issued on Nov. 22, 2023, in a counterpart European patent application.
Chinese Office Action mailed on Jan. 13, 2024 in a counterpart Chinese patent application.
Japanese Office Action mailed on Aug. 1, 2024 in a counterpart Japanese patent application No. JP 2023-201686.
Chinese Office Action mailed on Aug. 23, 2024 in counterpart Chinese patent application No. 201910919304.

* cited by examiner

FIG. 4

MEASUREMENT CONDITION FILE INFORMATION

| No. | CLASSIFICATION(1) | CLASSIFICATION(2) | ITEM NAME |
|---|---|---|---|
| 1 | BASIC MEASUREMENT INFORMATION | BASIC INFORMATION | BASIC MEASUREMENT CONDITION ID |
| 2 | | | MEASUREMENT CONDITION NAME |
| 3 | | | COMMENT |
| 4 | | MEASUREMENT INFORMATION | ANALYSIS AMOUNT |
| 5 | | | FLOW RATE |
| 6 | | | DILUTION RATIO |
| 7 | | THRESHOLD | THRESHOLD(FSC) |
| 8 | | | THRESHOLD(SSC) |
| 9 | | | THRESHOLD(FL1) |
| 10 | | | THRESHOLD(FL2) |
| 11 | | | THRESHOLD(FL3) |
| 12 | | | THRESHOLD(FL4) |
| 13 | INFORMATION ON DETECTION SENSITIVITY ADJUSTMENT | AMPLIFICATION VALUE | AMPLIFICATION VALUE(FSC) |
| 14 | | | AMPLIFICATION VALUE(SSC) |
| 15 | | PMT VOLTAGE | PMT VOLTAGE VALUE(FL1) |
| 16 | | | PMT VOLTAGE VALUE(FL2) |
| 17 | | | PMT VOLTAGE VALUE(FL3) |
| 18 | | | PMT VOLTAGE VALUE(FL4) |
| 19 | INFORMATION ON OPTICAL INFORMATION CORRECTION | FLUORESCENCE CORRECTION VALUE | FLUORESCENCE CORRECTION VALUE(FL1-FL2) |
| 20 | | | FLUORESCENCE CORRECTION VALUE(FL1-FL3) |
| 21 | | | FLUORESCENCE CORRECTION VALUE(FL1-FL4) |
| 22 | | | FLUORESCENCE CORRECTION VALUE(FL2-FL1) |
| 23 | | | FLUORESCENCE CORRECTION VALUE(FL2-FL3) |
| 24 | | | FLUORESCENCE CORRECTION VALUE(FL2-FL4) |
| 25 | | | FLUORESCENCE CORRECTION VALUE(FL3-FL1) |
| 26 | | | FLUORESCENCE CORRECTION VALUE(FL3-FL2) |
| 27 | | | FLUORESCENCE CORRECTION VALUE(FL3-FL4) |
| 28 | | | FLUORESCENCE CORRECTION VALUE(FL4-FL1) |
| 29 | | | FLUORESCENCE CORRECTION VALUE(FL4-FL2) |
| 30 | | | FLUORESCENCE CORRECTION VALUE(FL4-FL3) |
| 31 | INFORMATION ON GATING | INFORMATION ON SCATTERGRAM | SCATTERGRAM NAME |
| 32 | | | HIGHER-LEVEL GATE |
| 33 | | | X-AXIS ch |
| 34 | | | X-AXIS ch NAME |
| 35 | | | X-AXIS ch |
| 36 | | | X-AXIS ch NAME |
| 37 | | INFORMATION ON HISTOGRAM | HISTOGRAM NAME |
| 38 | | | HIGHER-LEVEL GATE |
| 39 | | | X-AXIS ch |
| 40 | | | X-AXIS ch NAME |
| 41 | | INFORMATION ON GATE | GATE NAME |
| 42 | | | POSITION INFORMATION |
| 43 | | | COLOR |
| 44 | | | MEASUREMENT ITEM NAME |
| 45 | | | UPPER LIMIT VALUE |
| 46 | | | LOWER LIMIT VALUE |
| 47 | | | RESULT VALUE TYPE |
| 48 | TEMPERATURE CORRECTION FORMULA | | |

FIG. 9

ASTM RECORD CONFIGURATION

| RECORD TYPE | RECORD IDENTIFIER | LEVEL |
|---|---|---|
| HEADER | H | 0 |
| PATIENT INFORMATION | P | 1 |
| QUERY | Q | 1 |
| MEASUREMENT REQUEST | O | 2 |
| MEASUREMENT RESULT | R | 3 |
| COMMENT | C | 1-4 |
| MANUFACTURER INFORMATION | M | 1-4 |
| SCIENTIFIC INFORMATION | S | N/A |
| MESSAGE STOP | L | 0 |

FIG. 10

ASTM FIELD 8 CONFIGURATION

| ASTM FIELD | FIELD NAME |
|---|---|
| 8.1.1 | RECORD FORMAT |
| 8.1.2 | SERIAL NUMBER |
| 8.1.3 | PATIENT ID ALLOCATED BY DOCTOR IN CHARGE |
| 8.1.4 | PATIENT ID ALLOCATED BY LABORATORY |
| 8.1.5 | PATIENT ID |
| 8.1.6 | PATIENT NAME |
| 8.1.7 | MOTHER'S MAIDEN NAME |
| 8.1.8 | DATE OF BIRTH |
| 8.1.9 | PATIENT SEX |
| 8.1.10 | PATIENT RACE |
| 8.1.11 | PATIENT ADDRESS |
| 8.1.12 | RESERVATION FIELD |
| 8.1.13 | PATIENT PHONE NUMBER |
| 8.1.14 | ID OF DOCTOR IN CHARGE |
| ... | ... |

FIG. 11

ASTM FIELD 10 CONFIGURATION

| ASTM FIELD | FIELD NAME |
|---|---|
| 10.1.1 | RECORD FORMAT |
| 10.1.2 | SERIAL NUMBER |
| 10.1.3 | MEASUREMENT ITEM ID |
| 10.1.4 | DATA VALUE |
| 10.1.5 | UNIT |
| 10.1.6 | UPPER AND LOWER LIMIT MANAGEMENT VALUE RANGE |
| 10.1.7 | MEASUREMENT RESULT ANOMALY FLAG |
| 10.1.8 | ANOMALY TEST KIND |
| 10.1.9 | MEASUREMENT RESULT STATUS |
| 10.1.10 | DATE OF STANDARD VALUE AND UNIT CHANGE |
| 10.1.11 | OPERATOR ID |
| 10.1.12 | MEASUREMENT START DATE AND TIME |
| 10.1.13 | MEASUREMENT COMPLETE DATE AND TIME |
| 10.1.14 | ANALYSIS DEVICE ID |

FIG. 12

COMMUNICATION DATA FORMAT OF DOT DATA

| ITEM (SUB FIELD) | SPECIFIC CONTENT OF ITEM |
|---|---|
| X AXIS NAME | INDICATE X AXIS NAME. |
| Y AXIS NAME | INDICATE Y AXIS NAME. |
| DATA X-AXIS SIZE | INDICATE MAXIMUM VALUE IN X-AXIS (HORIZONTAL) DIRECTION. SPECIFICALLY, INDICATE MAXIMUM VALUE OF DATA SET TO "XDISCRI 1 TO XDISCRI N". |
| DATA Y-AXIS SIZE | INDICATE MAXIMUM VALUE IN Y-AXIS (VERTICAL) DIRECTION. SPECIFICALLY, INDICATE MAXIMUM VALUE OF DATA SET TO "YDISCRI 1 TO YDISCRI N". |
| XRATIO | INDICATE RATIO FOR NORMALIZING X-AXIS SIGNAL. GRANULARITY DISTRIBUTION DATA IS CALCULATED AS PRODUCT OF DATA AT EACH DISCRETE POSITION OF "XDISCRI 1 TO XDISCRI N" AND "XRatio". |
| XDISCRI 1 | INDICATE SIGNAL STRENGTH OF XDISCRI 1 |
| XDISCRI 2 | INDICATE SIGNAL STRENGTH OF XDISCRI 2 |
| ... | ... |
| XDISCRI N | INDICATE SIGNAL STRENGTH OF XDISCRI N. OUTPUT IS MADE BY SIZE SPECIFIED BY DATA X-AXIS SIZE. |
| YRATIO | INDICATE RATIO FOR NORMALIZING Y-AXIS SIGNAL. GRANULARITY DISTRIBUTION DATA IS CALCULATED AS PRODUCT OF DATA AT EACH DISCRETE POSITION OF "YDISCRI 1 TO YDISCRI N" AND "YRatio". |
| YDISCRI 1 | INDICATE SIGNAL STRENGTH OF YDISCRI 1 |
| YDISCRI 2 | INDICATE SIGNAL STRENGTH OF YDISCRI 2 |
| ... | ... |
| YDISCRI N | INDICATE SIGNAL STRENGTH OF YDISCRI N. OUTPUT IS MADE BY SIZE SPECIFIED BY DATA Y-AXIS SIZE. |

FIG. 13

COMMUNICATION DATA FORMAT OF GRANULARITY DISTRIBUTION DATA

| ITEM (SUB FIELD) | SPECIFIC CONTENT OF ITEM |
|---|---|
| X AXIS NAME | INDICATE X AXIS NAME. |
| Y AXIS NAME | INDICATE Y AXIS NAME. |
| DATA X-AXIS SIZE | INDICATE NUMBER OF DATA IN X-AXIS (HORIZONTAL) DIRECTION. |
| DATA Y-AXIS SIZE | INDICATE MAXIMUM VALUE IN Y-AXIS (VERTICAL) DIRECTION. SPECIFICALLY, INDICATE MAXIMUM VALUE OF DATA SET TO "YDISCRI 1 TO YDISCRI N". |
| LOWER DISCRI | INDICATE LOWER LIMIT DISCRETE POSITION. FOR EXAMPLE, INDICATE THAT LOWER LIMIT DISCRETE POSITION IS POSITION OF "DISCRI 5" WHEN "LOWER DISCRI" VALUE IS FIVE.<br>VALUE "0" IS OUTPUT WITH NO LOWER LIMIT DISCRETE POSITION. |
| MIDDLE DISCRI | INDICATE MIDDLE DISCRETE POSITION. FOR EXAMPLE, INDICATE THAT MIDDLE DISCRETE POSITION IS POSITION OF "DISCRI 10" WHEN "MIDDLE DISCRI" VALUE IS 10.<br>VALUE "0" IS OUTPUT WITH NO MIDDLE DISCRETE POSITION. |
| UPPER DISCRI | INDICATE UPPER LIMIT DISCRETE POSITION. FOR EXAMPLE, INDICATE THAT UPPER LIMIT DISCRETE POSITION IS POSITION OF "DISCRI 25" WHEN "UPPER DISCRI" VALUE IS 25.<br>VALUE "0" IS OUTPUT WITH NO UPPER LIMIT DISCRETE POSITION. |
| RATIO (DIVISION RATIO) | INDICATE RATIO FOR NORMALIZATION. GRANULARITY DISTRIBUTION DATA IS CALCULATED AS PRODUCT OF DATA AT EACH DISCRETE POSITION OF "XDISCRI 1 TO XDISCRI 50" AND "Ratio". |
| DISCRI 1 | INDICATE FREQUENCY OF DISCRI 1. |
| DISCRI 2 | INDICATE FREQUENCY OF DISCRI 2. |
| ... | ... |
| DISCRI N | INDICATE FREQUENCY OF DISCRI N.<br>OUTPUT IS ADE BY SIZE SPECIFIED BY DATA X-AXIS SIZE. |

FLOW CYTOMETER, DATA TRANSMISSION METHOD, AND INFORMATION PROCESSING SYSTEM

CROSS REFERENCE TO RELATED APPLICATIONS

This application claims priority from to prior Japanese Patent Application No. 2018-179994 filed with the Japan Patent Office on Sep. 26, 2018 the entire contents of which are incorporated herein by reference.

BACKGROUND

The present disclosure relates to a flow cytometer, a data transmission method, and an information processing system.

Recently, an electronic medical record system that generates and manages an electronic medical record including various kinds of information of a patient, which is input by a doctor has been widely used.

The electronic medical record includes information of a patient such as full name, age, ID, kinds and dosages of therapeutic medicines, medical examination details, medical treatment details, an event such as an operation as well as a medical image such as an X-ray image or an ultrasonic wave image, and a test value output from a test device. As an electronic medical record system, known is a medical information system including at least one of a hospital information system (HIS) that supports hospital operations and a clinical laboratory information system (LIS) that supports clinical test operations.

Flow cytometry is known as a method that optically detects the size, structure, fluorescence intensity, and the like of each of particles dispersed in a liquid by using a flow cytometer capable of detecting each of particles, and measures the number and distribution of the particles based on the detected information.

The conventional electronic medical record system can acquire information indicating the numbers of blood cells such as lymphocytes, monocytes, and granulocytes as test values from a flow cytometry. The doctor can browse this information on the electronic medical record system. However, the conventional electronic medical record system does not support browsing of a particle distribution diagram illustrating particle distribution. This requires the doctor to browse the particle distribution diagram generated and managed at the flow cytometry from his/her own terminal device through a LAN ([searched on Jul. 12, 2018], the Internet <URL: https://www.bc-cytometry.com/FCM/FCM/fcm_08.html>(Non Patent Literature 1)).

As described above, in the conventional electronic medical record system as disclosed in Non Patent Literature 1, a doctor or an administrator such as a laboratory technician (for example, a chief engineer) needs to browse the particle distribution diagram managed at the flow cytometry from the terminal through the LAN. Thus, such a system has low operability for the doctor or the chief engineer (hereinafter referred to as "doctor or the like") to browse an electronic medical record including the particle distribution diagram, and accordingly is low in convenience.

Furthermore, the doctor or the like can browse the particle distribution diagram managed at the flow cytometry from the own terminal through the LAN, but is not allowed to make adjustment of the particle distribution diagram such as re-gating at the terminal. When the doctor or the like desires adjustment of the particle distribution diagram to achieve more accurate diagnosis, the doctor or the like needs to provide feedback about how to adjust to a laboratory technician or the like, and the laboratory technician or the like needs to generate another particle distribution diagram based on at least one of data which are managed at the flow cytometry and include particle data including optical information of particles contained in a sample and data on the particle distribution diagram of the particles generated based on the particle data. In this manner, in the conventional system, adjustment or the like of the particle distribution diagram requires time depending on the number of times of feedbacks between the doctor or the like and the laboratory technician or the like, which may disable the doctor or the like to perform accurate diagnosis quickly.

One or more aspects may provide a flow cytometer, a data transmission method, and an information processing system that can increase or improve the operability of an electronic medical record system in browsing an electronic medical record including a particle distribution diagram of particles contained in a sample to thus improve the convenience, and enable a doctor or the like to perform accurate diagnosis quickly.

SUMMARY

A flow cytometer according to one or more aspects may include: a particle data acquisition unit that measures particles in a sample to acquire particle data including optical information of the particles; and a transmission unit that transmits at least one of the particle data and data on a particle distribution diagram of the particles, generated based on the particle data, to at least one of a hospital information system that supports hospital operations and a clinical laboratory information system that supports clinical test operations.

A flow cytometer according to one or more aspects may include: a particle data acquisition unit that measures particles in a sample to acquire particle data including optical information of the particles; and a transmission unit that transmits the particle data.

A data transmission method according to one or more aspects may be executed by a computer. The method may include: measuring particles in a sample to acquire particle data including optical information of the particles; and transmitting at least one of the particle data and data on a particle distribution diagram of the particles, generated based on the particle data, to at least one of a hospital information system that supports hospital operations and a clinical laboratory information system that supports clinical test operations.

A data transmission method according to one or more aspects may be executed by a compute. The method may include: measuring particles in a sample to acquire particle data including optical information of the particles; and transmitting the particle data. An information processing system according to one or more aspects may include: a reception unit that receives at least one of: particle data that is acquired by measuring particles in a sample and includes optical information; and data on a particle distribution diagram of the particles, generated based on the particle data; and an electronic medical record generation unit that generates an electronic medical record including the particle distribution diagram based on the received at least one of the particle data and the data on the particle distribution diagram.

BRIEF DESCRIPTION OF DRAWINGS

FIG. 4 is a diagram illustrating exemplary information included in a measurement condition according to one or more embodiments, in which FSC represents forward scattered light, SSC represents side scattered light, FL1, FL2, FL3, and FL4 represent four kinds of fluorescence having different peak wavelengths, and ch represents channel;

FIG. 9 is a diagram illustrating an exemplary configuration of an ASTM record, such as in FIG. 8;

FIG. 10 is a diagram illustrating an exemplary configuration of an ASTM field, such as in FIG. 8;

FIG. 11 is a diagram illustrating an exemplary configuration of an ASTM field, such as in FIG. 8;

FIG. 12 is a diagram illustrating an exemplary communication data format of dot data included and transmitted in "data value," such as of an ASTM field 10.1.4 illustrated in FIG. 11;

FIG. 13 is a diagram illustrating an exemplary communication data format of granularity distribution data included and transmitted in "data value," such as of an ASTM field 10.1.4 illustrated in FIG. 11.

DETAILED DESCRIPTION

Figure 1:
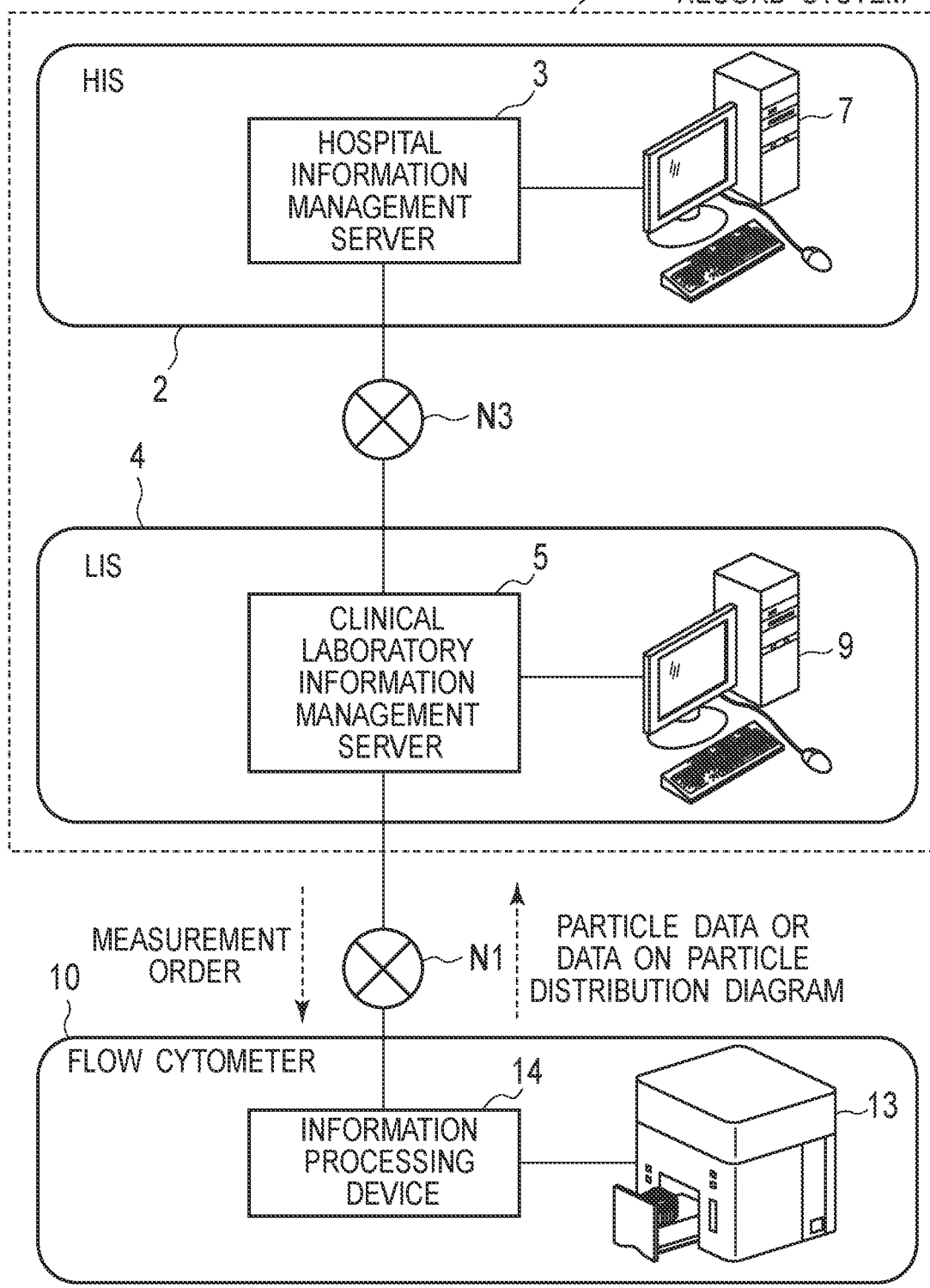
FIG. 1 is a diagram illustrating an exemplary schematic diagram of a network configuration of a flow cytometer and an electronic medical record system according to one or more embodiments.

A flow cytometer (10) according to one or more aspects includes: a particle data acquisition unit (633) that measures particles contained in a sample to acquire particle data including optical information of the particles; and a transmission unit (635) that transmits at least one of the particle data and data on a particle distribution diagram of the particles, which is generated based on the particle data, to at least one of a hospital information system (2) that supports hospital operations and a clinical laboratory information system (4) that supports clinical test operations.

With the above-described flow cytometer (10), at least one of particle data including optical information of particles contained in a sample and data on a particle distribution diagram of the particles generated based on the particle data is transmitted to at least one of the hospital information system (2) and the clinical laboratory information system (4). With this configuration, an electronic medical record including a particle distribution diagram of particles contained in a sample can be generated in at least one of the hospital information system (2) and the clinical laboratory information system (4), and the generated electronic medical record can be browsed. In addition, the particle distribution diagram in the electronic medical record can be adjusted as necessary. Accordingly, it is possible to increase system operability in browsing the electronic medical record to improve the convenience, and in addition, to enable a doctor or the like to perform accurate diagnosis quickly.

A flow cytometer (10) according to one or more aspects includes: a particle data acquisition unit (633) that measures particles contained in a sample to acquire particle data including optical information of the particles; and a transmission unit (635) that transmits the particle data.

With the above-described flow cytometer (10), particle data including optical information of particles contained in a sample is transmitted. With this configuration, an electronic medical record including a particle distribution diagram of particles contained in a sample can be generated and browsed at the destination of the particle data. In addition, the particle distribution diagram in the electronic medical record can be adjusted as necessary. Accordingly, it is possible to increase the operability in browsing the electronic medical record to thus improve the convenience, and in addition, to enable a doctor or the like to perform accurate diagnosis quickly.

The above-described flow cytometer (10) may further include an order information acquisition unit (631) that acquires order information including one or more measurement items, and the particle data acquisition unit (633) may measure the particles contained in the sample in accordance with the one or more measurement items included in the order information.

With the above-described flow cytometer (10), the particles contained in the sample can be measured in accordance with the one or more measurement items included in the order information, and thus a measurement result in accordance with each measurement item can be acquired.

In the above-described flow cytometer (10), after pretreatment of preparing a measurement specimen from the sample is executed, the particle data acquisition unit (633) may measure the particles contained in the measurement specimen.

With the above-described flow cytometer (10), it is possible to perform particle measurement more suitable for a measurement item included in a measurement order by executing pretreatment of preparing a measurement specimen from the sample, and thus accurate particle data can be acquired.

In the above-described flow cytometer (10), the transmission unit (635) may transmit output information for use to output the particle distribution diagram of the particles based on the particle data, as the data on the particle distribution diagram, to at least one of the hospital information system (2) that supports hospital operations and the clinical laboratory information system (4) that supports clinical test operations.

With the above-described flow cytometer (10), image data corresponding to the particle distribution diagram does not need to be transmitted, and thus it is possible to reduce the amount of transmitted data.

In the above-described flow cytometer (10), the output information may include output information for use to output a plurality of the particle distribution diagrams different from each other based on the particle data.

With the above-described flow cytometer (10), it is possible to display, in comparison, particle distribution diagrams corresponding to particle data measured for a sample on different dates and times.

In the above-described flow cytometer (10), the output information may further include date and time information including date and time at which the particles contained in the sample are measured.

With the above-described flow cytometer (10), it is possible to display, in a temporal sequence, particle distribution diagrams corresponding to particle data for a sample.

In the above-described flow cytometer (10), the optical information may include at least one of scattered light information and fluorescence information of the particles.

With the above-described flow cytometer (10), when having acquired at least one of scattered light information and fluorescence information of the particles, at least one of the hospital information system (2) and the clinical laboratory information system (4) can convert the information into data based on which a particle distribution diagram can be output, and can output an electronic medical record including the particle distribution diagram.

In the above-described flow cytometer (10), the transmission unit (635) may transmit, in a format compliant with a predetermined standard, at least one of the particle data and data on a particle distribution diagram of the particles generated based on the particle data.

With the above-described flow cytometer (10), data is transmitted in a format compliant with a predetermined standard, and thus can be reliably transmitted.

In the above-described flow cytometer (10), the predetermined standard may be a standard compliant with Clinical and Laboratory Standards Institute (CLSI).

With the above-described flow cytometer (10), data is transmitted in a format compliant with CLSI as an international standard, and thus can be reliably transmitted.

In the above-described flow cytometer (10), the predetermined standard may include at least one of standards of American Society for Testing and Materials (ASTM), Health Level Seven (HL7), Integrating the Healthcare Enterprise (IHE), Digital Imaging and Communications in Medicine (DICOM), and Medical waveform Format Encoding Rules (MFER).

With the above-described flow cytometer (10), it is possible to use various standards related to information communication, and thus the range of selection related to the format of data transmission is increased.

In the above-described flow cytometer (10), the transmission unit (635) may further transmit patient information associated with the sample to at least one of the hospital information system (2) that supports hospital operations and the clinical laboratory information system (4) that supports clinical test operations.

With the above-described flow cytometer (10), a sample associated with a particular patient can be identified in at least one of the hospital information system (2) and the clinical laboratory information system (4).

In the above-described flow cytometer (10), the patient information may include patient identification information that identifies a patient.

With the above-described flow cytometer (10), a sample associated with a particular patient can be more accurately identified in at least one of the hospital information system (2) and the clinical laboratory information system (4).

In the above-described flow cytometer (10), the transmission unit (635) may transmit or send, for each sample, a message including patient information associated with the sample and at least one of the particle data and data on a particle distribution diagram of the particles, which is generated based on the particle data, to at least one of a the hospital information system (2) that supports hospital operations and a the clinical laboratory information system (4) that supports clinical test operations.

With the above-described flow cytometer (10), for each sample, at least one of particle data and data on a particle distribution diagram is transmitted in association with patient information, and thus it is possible to accurately output an electronic medical record of a patient that a doctor desires to browse.

In the above-described flow cytometer (10), the message may include a first record including at least one of the particle data and the data on the particle distribution diagram, and a second record including the patient information.

With the above-described flow cytometer (10), at least one of particle data and data on a particle distribution diagram is transmitted in association with patient information, and thus it is possible to accurately output an electronic medical record of a patient that a doctor desires to browse.

In the above-described flow cytometer (10), the transmission unit (635) may transmit at least one of the particle data and the data on the particle distribution diagram to the hospital information system (2) that supports hospital operations through the clinical laboratory information system (4) that supports clinical test operations.

With the above-described flow cytometer (10), data can be transmitted through or via the clinical laboratory information system (4) when the flow cytometer (10) is not directly connected with the hospital information system (2).

In the above-described flow cytometer (10), the particle distribution diagram of the particles generated based on the particle data may include at least one of a dot plot and a histogram.

With the above-described flow cytometer (10), data of particles contained in a sample is displayed in at least one of a dot plot and a histogram, and thus it is possible to appropriately understand the distribution state of the particles.

In the above-described flow cytometer (10), the transmission unit (635) may transmit compressed data including at least one of the particle data and data on a particle distribution diagram of the particles generated based on the particle data to at least one of the hospital information system (2) that supports hospital operations and the clinical laboratory information system (4) that supports clinical test operations.

With the above-described flow cytometer (10), transmission data to at least one of the hospital information system (2) and the clinical laboratory information system (4) is compressed, and thus it is possible to reduce the amount of data at transmission.

In the above-described flow cytometer (10), the transmission unit (635) may further transmit particle number information on the number of the particles.

With the above-described flow cytometer, the transmission unit (635) further transmits the particle number information on the number of the particles, and thus it is possible to generate and output an electronic medical record further including the number of particles as a test value.

A data transmission method executed by a computer according to one or more aspects includes: measuring particles contained in a sample to acquire particle data including optical information of the particles; and transmitting at least one of the particle data and the data on the particle distribution diagram of the particles generated based on the particle data to at least one of a the hospital information system (2) that supports hospital operations and a the clinical laboratory information system (4) that supports clinical test operations.

With the above-described data transmission method, at least one of particle data of particles contained in a sample and the data on the particle distribution diagram of the particles generated based on the particle data is transmitted to at least one of the hospital information system (2) and the clinical laboratory information system (4). With this configuration, an electronic medical record including a particle distribution diagram of particles contained in a sample can be generated in at least one of the hospital information system (2) and the clinical laboratory information system (4), and the generated electronic medical record can be browsed. Accordingly, it is possible to increase system operability in browsing the electronic medical record to thus improve the convenience, and in addition, to enable a doctor or the like to perform accurate diagnosis quickly.

A data transmission method executed by a computer according to one or more aspects includes: measuring particles contained in a sample to acquire particle data including optical information of the particles; and transmitting the particle data.

With the above-described data transmission method, particle data of particles contained in a sample is transmitted. With this configuration, an electronic medical record including a particle distribution diagram of particles contained in a sample can be generated and browsed at the destination of the particle data. In addition, the particle distribution diagram in the electronic medical record can be adjusted as necessary. Accordingly, it is possible to increase the operability in browsing the electronic medical record to thus improve the convenience, and in addition, to enable a doctor or the like to perform accurate diagnosis quickly.

An information processing system according to one or more aspects includes: a reception unit that receives at least one of particle data acquired by measuring particles contained in a sample and including optical information, and data on a particle distribution diagram of the particles generated based on the particle data; and an electronic medical record generation unit that generates an electronic medical record including the particle distribution diagram based on the received at least one of the particle data and the data on the particle distribution diagram.

With the above-described information processing system, at least one of particle data including optical information of particles contained in a sample and data on a particle distribution diagram of the particles generated based on the particle data is received, and an electronic medical record including a particle distribution diagram of particles contained in a sample is generated. In addition, the particle distribution diagram in the electronic medical record can be adjusted as necessary. With this configuration, the generated electronic medical record can be browsed, and thus it is possible to increase system operability in browsing the electronic medical record to thus improve the convenience, and in addition, to enable a doctor or the like to perform accurate diagnosis quickly.

The present disclosure may provide a flow cytometer, a data transmission method, and an information processing system that can increase the operability of an electronic medical record system in browsing an electronic medical record including a particle distribution diagram of particles contained in a sample to thus improve the convenience, and enable a doctor or the like to perform accurate diagnosis quickly.

Embodiments are described below with the accompanying drawings. In the drawings, components denoted by an identical reference sign have identical or similar configurations.

[Flow Cytometer and Electronic Medical Record System]

FIG. 1 is a diagram illustrating an exemplary schematic diagram of a network configuration of a flow cytometer and an electronic medical record system according to one or more embodiments. This flow cytometer 10 illustrated in FIG. 1 is a measurement device used to perform flow cytometry as a method of optically detecting the size, structure, fluorescence intensity, and the like of each of particles dispersed in liquid and measuring the number of and distribution the particles based on the detected information. For example, the flow cytometer 10 has a function of detecting individual particles by a sheath flow scheme.

As illustrated in FIG. 1, the flow cytometer 10 is installed at, for example, a hospital or a test facility and includes, as an example, a flow cytometer body 13 and an information processing device 14 connected with the flow cytometer body 13. Specific configurations of the flow cytometer body 13 and the information processing device 14 will be described later. The electronic medical record system 1 (information processing system) collects information on a test result obtained from the flow cytometer 10 as well as various kinds of information such as the full name, age, ID, therapeutic medicine kind and dosage amount, medical examination details, medical treatment details, treatment details, disease name, various medical test orders, and an event such as an operation of a patient, and generates and manages an electronic medical record.

The flow cytometer 10 is connected with the electronic medical record system 1 through a communication network N1. The communication network N1 is a communication medium such as the Internet, a virtual private network (VPN), a wide area communication network (WAN), or a public switched telephone network (PSTN) but not limited thereto, and may be any network through which communication can be performed between the flow cytometer 10 and the electronic medical record system 1.

The following describes the overview of one or more embodiments. As illustrated in FIG. 1, the flow cytometer 10 acquires a measurement order (order information) including one or more measurement items from the electronic medical record system 1, and measures particles contained in a sample in accordance with the one or more measurement items included in the measurement order. The flow cytometer 10 measures particles contained in the sample to acquire particle data including optical information of the particles, and transmits, to the electronic medical record system 1, at least one of the acquired particle data and data on a particle distribution diagram of the particles generated based on the acquired particle data. The flow cytometer 10 may measure particles contained in the sample to acquire particle data including optical information of particles, and may transmit only the acquired particle data to the electronic medical record system 1.

The measurement items included in the measurement order are one or more items measured by the flow cytometer 10, and are, for example, the kind of particle, and the kind of material existing at particles. Examples of the items include the kind of cell, the kind of protein, the kind of sugar chain, the kind of lipid, the kind of glycoprotein, the kind of glycolipid, the kind of lipoprotein, and the kind of nucleic acid. As described later, the measurement order may include a measurement condition of measurement at the flow cytometer 10.

Particle data is data on particles and includes, for example, optical information of the particles. The optical information is information included in one or more light wavelength spectra emitted from the particles. Each light wavelength spectrum includes an individual light wavelength and an individual light wavelength region included in the light wavelength spectrum, and the strength of each light wavelength or each light wavelength region. The individual light wavelength and the individual wavelength region can be specified based on which of one or more light receiving elements (for example, refer to light receiving elements 100A to 100F in FIG. 5) to be described later has received the light. The strength of each light wavelength or light wavelength region can be specified based on an electric signal output from a light receiving element having received the light. As an example, the optical information includes forward scattered light information indicating the size of a cell (particle), side scattered light information indicating the internal structure of the cell, and fluorescence information indicating development of protein, gene, or the like in the cell. When having acquired particle data including the optical information of the particles from the flow cytometer 10, the electronic medical record system 1 converts the acquired particle data into data based on which a particle distribution diagram can be output, and generates and outputs an electronic medical record including the particle distribution diagram.

The particle data may further include particle number information on the number of the particles. The particle number information includes, for example, the number of blood cells such as lymphocytes, monocytes, and granulocytes.

Data on a particle distribution diagram includes, for example, (1) output information for outputting the particle distribution diagram at the electronic medical record system 1, and (2) image data representing the particle distribution diagram. When having acquired, from the flow cytometer 10, (1) the output information outputting the particle distribution diagram at the electronic medical record system 1, the electronic medical record system 1 generates and outputs an electronic medical record including the particle distribution diagram based on the acquired output information. The output information for outputting the particle distribution diagram at the electronic medical record system 1 includes (1-1) dot data (refer to FIG. 12 to be described later) corresponding to the particle data of each particle measured by the flow cytometer 10, and (1-2) granularity distribution data (refer to FIG. 13 to be described later) corresponding to distribution of particles measured by the flow cytometer 10. When having acquired (2) the image data representing the particle distribution diagram from the flow cytometer 10, the electronic medical record system 1 generates and outputs an electronic medical record including a particle size distribution diagram corresponding to the acquired image data.

In this manner, the flow cytometer 10 transmits at least one of the particle data of particles contained in a sample and data on the particle distribution diagram of the particles generated based on the particle data to the electronic medical record system 1. With this configuration, an electronic medical record including the particle distribution diagram of particles contained in a sample can be generated in the electronic medical record system 1 and browsed at, for example, a doctor terminal device 7 or a laboratory technician terminal device 9 of the electronic medical record system 1. In addition, the particle distribution diagram in the electronic medical record can be adjusted as necessary. Thus, it is possible to increase the operability in browsing the electronic medical record to thus improve the convenience, and in addition, to enable a doctor or the like to perform accurate diagnosis quickly.

As illustrated in FIG. 1, as an example, the electronic medical record system 1 includes a hospital information system (HIS) 2 that supports hospital operations, and a clinical laboratory information system (LIS) 4 that supports clinical test operations.

As an example, the HIS 2 includes a hospital information management server 3 having, for example, a function of electrically managing an instruction (order) for a test, prescription, or the like performed by a doctor or a nurse, medical accounting function, and a function (electronic medical record generation unit) of generating and managing an electronic medical record, and the doctor terminal device 7 that displays an electronic medical record to be browsed by, for example, a doctor.

The LIS 4 is an information system that handles general test operations performed by a laboratory technician or the like at a medical facility such as a hospital, and includes a clinical laboratory information management server 5 having, for example, a function of accepting a test, a function of reporting a test result, and a function of supporting a test flow such as data management, and the laboratory technician terminal device 9 that displays, for example, a screen on which a laboratory technician browses test details. The LIS 4 may have a function (electronic medical record generation unit) of generating and managing an electronic medical record.

As described above, a measurement order is transmitted from the electronic medical record system 1 to a flow cytometry 10, but may be transmitted from the HIS 2 through the LIS 4 based on, for example, an instruction from a doctor. Alternatively, the measurement order may be transmitted from the LIS 4 to the flow cytometry 10 based on, for example, an instruction from a laboratory technician.

As illustrated in FIG. 1, the HIS 2 and the LIS 4 are connected with each other through a communication network N3. The communication network N3 is a communication medium such as the Internet, a virtual private network (VPN), a wide area communication network (WAN), or a public switched telephone network (PSTN) but not limited thereto, and may be any network through which communication can be performed between the HIS 2 and the LIS 4.

The number of flow cytometers 10 connected with the electronic medical record system 1 is not limited, but a plurality of flow cytometers 10 may be connected with the electronic medical record system 1. In addition, the numbers of HISs 2 and LISs 4 included in the electronic medical record system 1 are not particularly limited.

Figure 2:
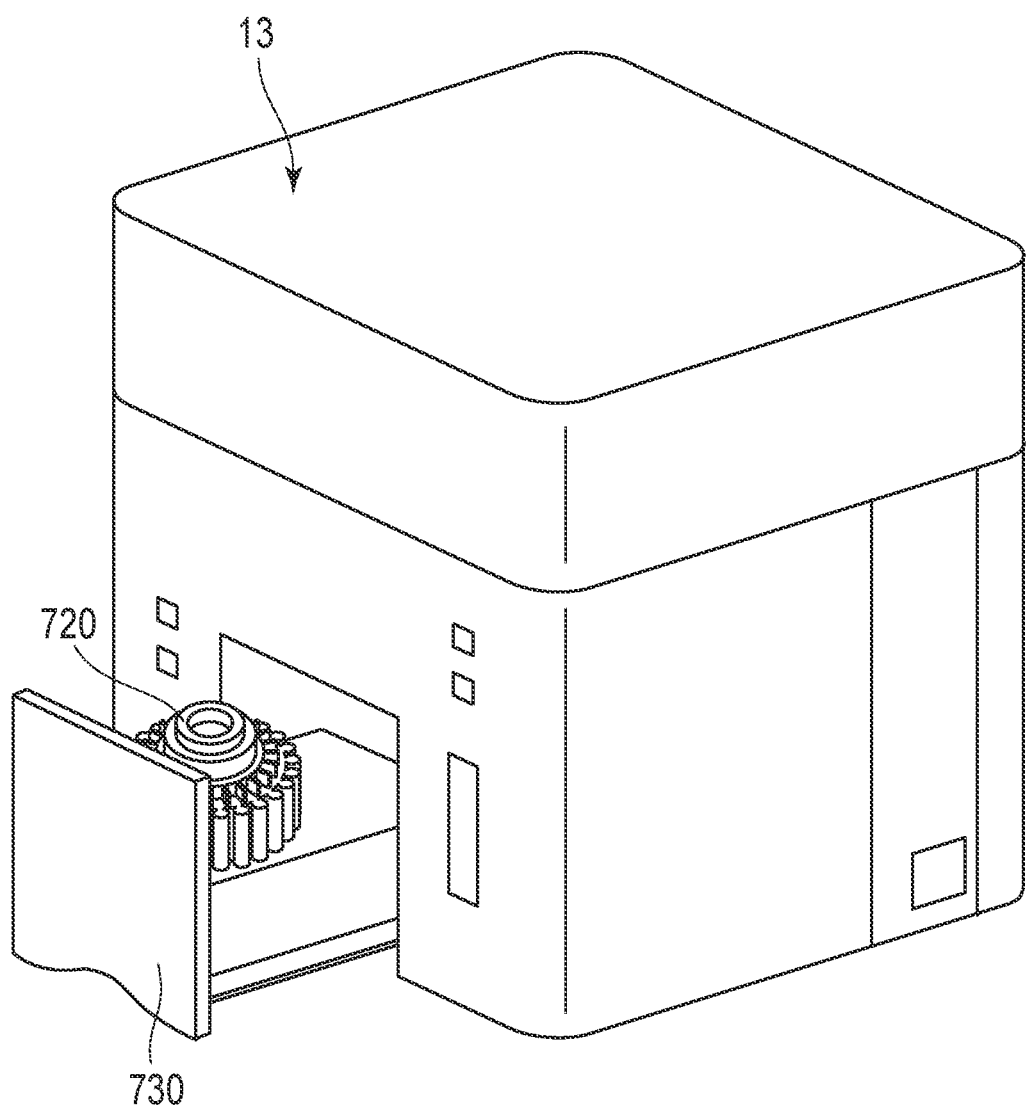
FIG. 2 is a diagram illustrating an exemplary exterior diagram of a flow cytometer according to one or more embodiments.

FIG. 2 is a diagram illustrating an exemplary exterior diagram of the flow cytometer according to one or more embodiments. As illustrated in FIG. 2, as an example, the flow cytometer body 13 includes a housing unit 730 housing a specimen container 720 in which a measurement specimen prepared through pretreatment is housed, and an aspiration unit (not illustrated) that can elevate and horizontally move. For example, as illustrated in FIG. 2, the specimen container 720 is positioned inside the flow cytometer body 13 by placing the specimen container 720 in the housing unit 730 and moving the housing unit 730 into the flow cytometer body 13. Then, measurement of the measurement specimen in the specimen container 720 is instructed to the flow cytometer. Accordingly, the aspiration unit aspirates the measurement specimen from the specimen container 720 positioned inside the flow cytometer body 13.

[Optical System of Flow Cytometer]

Figure 3:
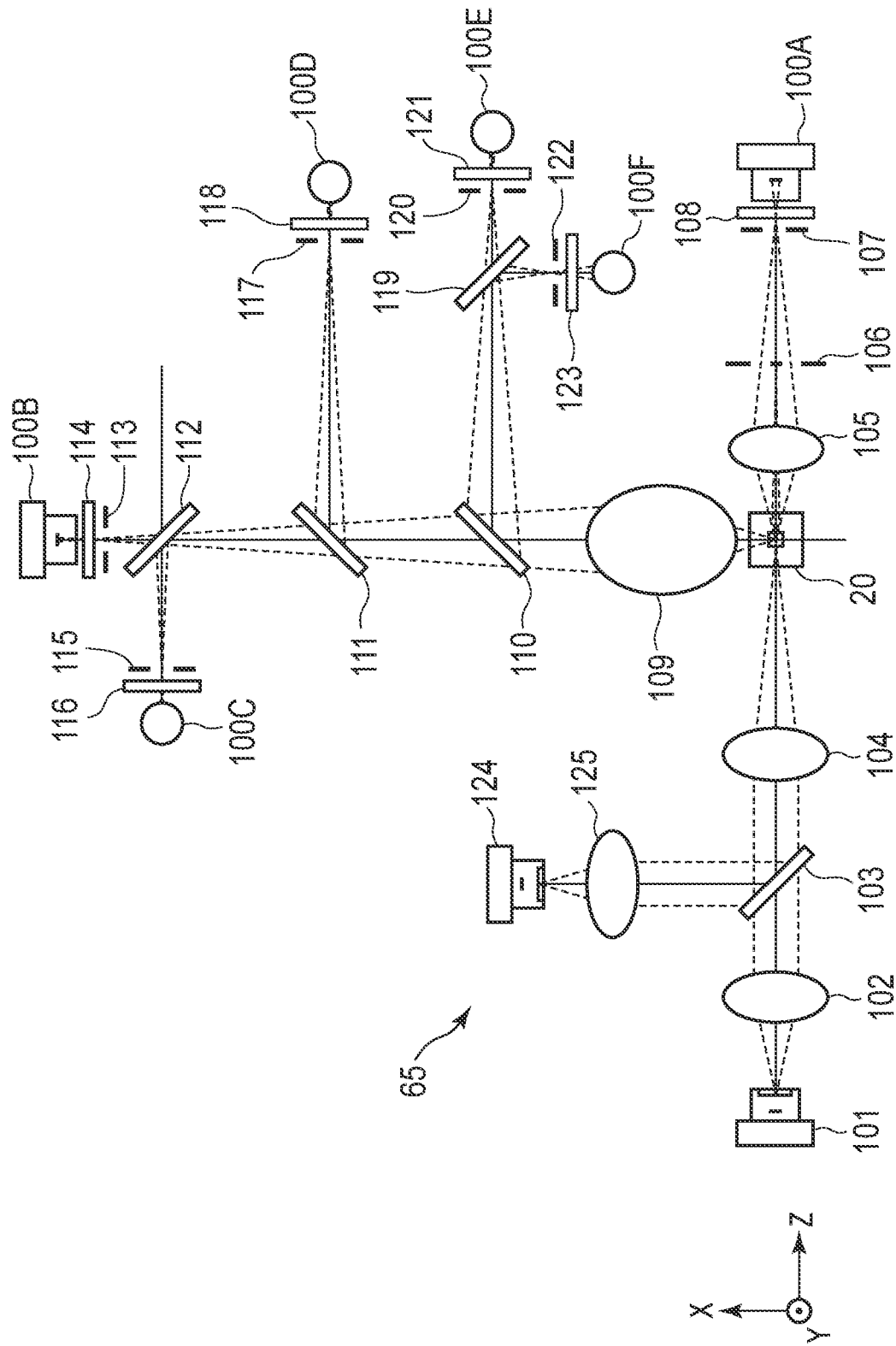
FIG. 3 is a diagram illustrating an exemplary optical system of a flow cytometer according to one or more embodiments.

FIG. 3 is a diagram illustrating an exemplary optical system of the flow cytometer according to one or more embodiments. The flow cytometer 10 includes a flow cell 20 through which particle-containing liquid containing particles in a sample passes, light sources 101 and 124 that emit light onto the particles passing through the flow cell 20, and light receiving elements 100A to 100F that detect the optical information of particle-attributable light, or light emitted from a particle, and output a detection signal converted into an electric signal.

The particles preferably emit one or a plurality of kinds of light when irradiated with predetermined light. Light emitted from the particles when irradiated with the predetermined light is collectively referred to as particle-attributable light. The particle-attributable light includes scattered light, emitted light, and the like. The particle-attributable light may be light having any wavelength, but is preferably light having a peak wavelength in the range of 400 nm to 850 nm. More specifically, the particle-attributable light is preferably fluorescence. The particle-attributable light may be emitted light, such as autofluorescence, attributable to material contained in the particles. Alternatively, the particles may be labeled with a light emission material such as fluorescent substance, and light emitted from the light emission material may be detected as the particle-attributable light. The peak wavelength of the particle-attributable light is preferably different between measurement items.

The particle-containing liquid includes particle suspension aspirated from the specimen into the flow cytometer, and contains diluent as necessary.

The following specifically describes examples in which the particle-attributable light is scattered light and fluorescence. Light emitted from the light source 101 is incident on the flow cell 20 through a collimate lens 102, a dichroic mirror 103, and a condenser lens 104. Forward scattered light of the particle-attributable light passing through the flow cell 20 is condensed through a condenser lens 105 and incident on the light receiving element 100A through a beam stopper 106, a pin-hole plate 107, and a band-pass filter 108.

Side scattered light and side fluorescence and the particle-attributable light passing through the flow cell 20 is condensed through a condenser lens 109. The side scattered light is incident on the light receiving element 100B through dichroic mirrors 110, 111, and 112, a pin-hole plate 103, and a band-pass filter 114. The side fluorescence having a wavelength of 520 nm to 542 nm inclusive transmits through the dichroic mirrors 110 and 111 and is reflected by the dichroic mirror 112 and incident on the light receiving element 100C through a pin-hole plate 115 and a band-pass filter 116. The side fluorescence having a wavelength of 570 nm to 620 nm inclusive transmits through the dichroic mirror 110 and is reflected by the dichroic mirror 111 and incident on the light receiving element 100D through a pin-hole plate 117 and a band-pass filter 118. The side fluorescence having a wavelength of 670 nm to 800 nm inclusive is reflected by the dichroic mirror 110, transmits through a dichroic mirror 119, and is incident on the light receiving element 100E through a pin-hole plate 120 and a band-pass filter 121.

Light emitted from a light source 124 is incident on the flow cell 20 through a collimate lens 125, the dichroic mirror 103, and the condenser lens 104. Side fluorescence of the particle-attributable light passing through the flow cell 20 is condensed through the condenser lens 109. The side fluorescence having a wavelength of 662.5 nm to 687.5 nm inclusive is reflected by the dichroic mirror 110 and the dichroic mirror 119 and then incident on the light receiving element 100F through a pin-hole plate 122 and a band-pass filter 123.

In one or more embodiments, for example, the light source 101 is a laser diode having a wavelength of 488 nm, and the light source 124 is a laser diode having a wavelength of 642 nm. The flow cell 20 is a sheath flow cell. The light receiving element 100A, which receives forward scattered light, is a photodiode, the light receiving element 100B, which receives side scattered light, is an avalanche photodiode (APD), and the light receiving elements 100C to 100F, which receive side fluorescence, are photomultiplier tubes (PMTs). In one or more embodiments, the flow cytometer 10 includes the six light receiving elements 100A to 100F. The four light receiving elements 100C to 100F detect the optical information of four respective kinds of light having different peak wavelengths attributable to pigments coupled with particles in the specimen, but are not limited thereto. For example, when the flow cytometer 10 includes three or more light receiving elements, at least two of the three or more light receiving elements may detect the optical information of respective kinds of light attributable to at least two pigments having different peak wavelengths. For example, in a HIV test, when four kinds of labeling antibody pigments coupled with CD4, CD45, CD8, and CD3, respectively, on a cell surface are used, four kinds of fluorescence having four peak wavelengths attributable to the respective labeling antibody pigments in response to markers existing on the cell surface are generated from the measurement specimen and can be detected by the four light receiving elements 100C to 100F.

The number of light sources may be one or equal to or larger than two. Each light source is selected in accordance with the wavelength region of light attributable to a pigment coupled with a particle. When the number of light sources is equal to or larger than two, these light sources preferably emit light having different peak wavelengths. The number of light sources is preferably equal to or larger than two because a plurality of kinds of fluorescence can be accurately separated and detected as compared to a case in which the number of light sources is one. For example, when one light source is used in a HIV test, FITC is used as a labeling antibody pigment for CD4 and PEcy5 is used as a labeling antibody pigment for CD8 in some cases. Since the peak wavelength of fluorescence from the FITC and the peak wavelength of fluorescence from the PEcy5 are close to each other, the overlapping part of the wavelength regions thereof tends to be large. However, when two light sources are used, a plurality of kinds of fluorescence can be separated and detected by shifting the timings of light emission from the light sources. In addition, the overlapping part of the wavelength regions of a plurality of kinds of fluorescence can be reduced by using a pigment suitable for the peak wavelength of light from each light source. For example, in place of PEcy5, APC can be used as the labeling antibody pigment for CD8. The numbers of photodiodes, dichroic mirrors, and band-pass filters are can be changed in accordance with the number of peak wavelengths of the particle-attributable light. In addition, the kinds of photodiode, dichroic mirror, and band-pass filter can be selected in accordance with the peak wavelength or wavelength region of the particle-attributable light, and the strength thereof.

Figure 5:
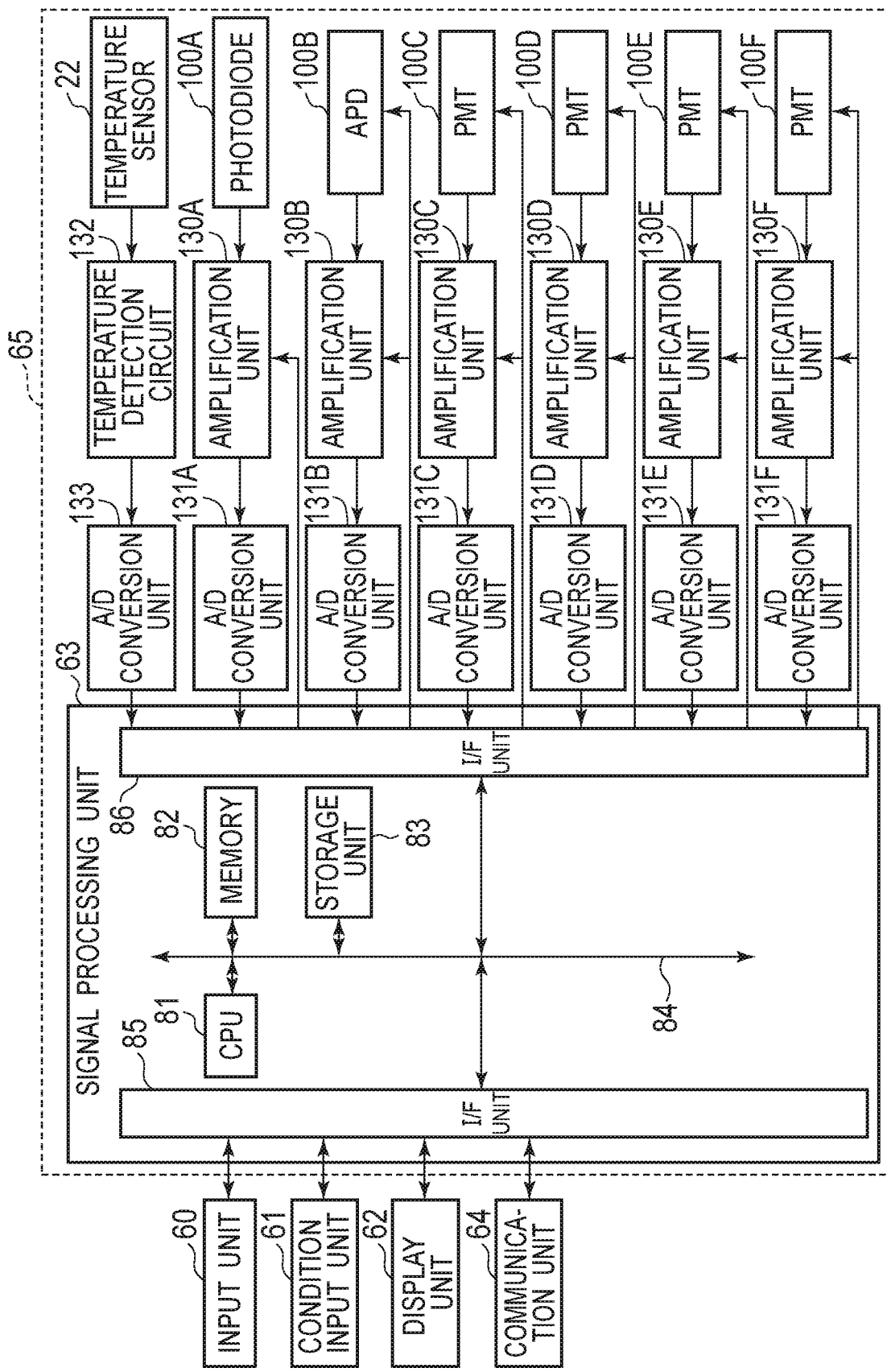
FIG. 5 is a diagram illustrating an exemplary information processing system of a flow cytometer according to one or more embodiments.

As illustrated in FIG. 5 to be described later, the detection signals output from the respective light receiving elements 100A to 100F are amplified by amplification units 130A to 130F, A/D converted by A/D conversion units 131A to 131F, and input to a signal processing unit 63. Specifically, the amplification units 130A and 130B connected with the light receiving element 100A as a photodiode and the light receiving element 100B as an APD are known amplification circuits such as operational amplifiers, and adjust the output voltages of the light receiving elements 100A and 100B, which are input thereto, by adjusting the degree of amplification at each amplification circuit. In addition, the values of voltage applied to the light receiving elements 100C to 100F as PMTs are changed to adjust the output voltages of the PMTs. Hereinafter, adjustment of the detection sensitivities of the light receiving elements 100A to 100F is adjustment of the degree of amplification of amplification circuits at the light receiving elements 100A and 100B, and adjustment of voltages applied to the light receiving elements 100C to 100F at the light receiving elements 100C to 100F. The detection signals output from the light receiving elements 100A and 100B are amplified by adjusting the degree of amplification of amplification circuits at the light receiving elements, and the detection signals output from the light receiving elements 100C to 100F are adjusted by adjusting the voltages applied to the light receiving elements 100C to 100F. Amplification includes a case in which the ratio of an output signal relative to an input signal is equal to or larger than one and a case in which the ratio is smaller than one. The amplification units 130C to 130F connected with the light receiving elements 100C to 100F may further include known amplification circuits, and adjustment of the detection sensitivities of the light receiving elements 100C to 100F may include adjustment of the output voltages of the light receiving elements 100C to 100F by these amplification circuits.

As an example, the flow cytometer 10 includes, in addition to the configuration including the light source 124, the flow cell 20, and the light receiving elements 100A to 100F, which is illustrated in FIG. 2, a measurement unit 65 including the amplification units 130A to 130F, the A/D conversion units 131A to 131F, the signal processing unit 63, and a temperature sensor 22 to be described later, which are illustrated in FIG. 5. The measurement unit 65 optically measures particles in the particle-containing liquid passing through the flow cell 20 in accordance with a measurement condition received by a communication unit 64 to be described later. The measurement includes detection of the optical information of the particle-attributable light by the light receiving elements 100A to 100F, and storage of the detection signals output from the light receiving elements 100A to 100F. The measurement also includes processing performed by the signal processing unit 63 to be described later, such as generation of a result of measurement of the number of particles or the like by using the stored detection signals. The detection signals output from the light receiving elements 100A to 100F include signals output from the A/D conversion units 131A to 131F through the amplification units 130A to 130F.

As illustrated in FIG. 1, the flow cytometer 10 includes the flow cytometer body 13, and the information processing device 14 connected with the flow cytometer body 13. The configuration including the light source 124, the flow cell 20, and the light receiving elements 100A to 100F, which is illustrated in FIG. 2, and the amplification units 130A to 130F, and the A/D conversion units 131A to 131F in the measurement unit 65 are disposed in the flow cytometer body 13. The signal processing unit 63 is disposed in the information processing device 14. When the flow cytometer 10 includes no information processing device 14, the signal processing unit 63 may be disposed in the flow cytometer body 13. The flow cytometer 10 also includes a controller that controls a pump, a motor, or the like (not illustrated) for causing the particle-containing liquid to pass through the flow cell 20 to perform measurement, but the controller may be achieved by the signal processing unit 63, and may be separately disposed in the information processing device 14 or the flow cytometer body 13.

[Measurement Condition]

To set a measurement condition in accordance with measurement items before measurement, the flow cytometer 10 receives a measurement condition included in the measurement order, for example, from the electronic medical record system 1 illustrated in FIG. 1. The flow cytometer 10 may receive a measurement condition from an external server (not illustrated). FIG. 4 exemplarily illustrates information included in the received measurement condition when the particle-attributable light is fluorescence. The measurement condition includes basic information on measurement (hereinafter referred to as "basic measurement information"), information on adjustment of the detection sensitivity for detecting the optical information (hereinafter referred to as "detection sensitivity adjustment related information"), information on correction of the detected optical information, gating related information for setting a selected particle region based on the optical information (hereinafter referred to as "gating related information"), and a formula used for temperature correction to be described later.

The basic measurement information includes basic information, measurement information, and a threshold. The basic information includes identification information (referred to as "measurement condition ID" in FIG. 4) for specifying the kind of measurement condition and a measurement condition name. The measurement information includes the analysis amount of the specimen aspirated into the flow cytometer, a flow rate indicating a flow speed at which particles flow into the flow cytometer, and the dilution ratio of the specimen aspirated into the flow cytometer. The threshold is also called a sensing level, and is the lower limit set value of the optical information detected as a particle. The light receiving elements 100A to 100F each set the threshold for the light attributable to particles. For example, the threshold can be set in the numerical value range of 0 to 1023 in accordance with the intensity of light. When the threshold is set to be 50, light having an intensity of 50 or higher is detected as a particle.

The detection sensitivity adjustment related information includes at least one of a value indicating the degree of amplification of the output voltage of each of the light receiving elements 100A to 100F and the value of voltage applied to each of the light receiving elements 100A to 100F. For example, the detection sensitivity adjustment related information includes an amplification value for adjusting the degree of amplification at each of amplification circuits connected with the light receiving elements 100A and 100B and a PMT voltage value for adjusting voltage applied to each of the light receiving elements 100C to 100F. The detection sensitivity adjustment related information may include only any one of the amplification value and the PMT voltage value. When amplification circuits are connected with the light receiving elements 100C to 100F, the detection sensitivity adjustment related information may include an amplification value adjusting the degree of amplification at each amplification circuit.

The information on correction of the detected optical information includes information on the distribution amount of light wavelengths not to be detected, which is included in the optical information detected by the light receiving elements 100A to 100F. When two or more kinds of light emitted from particles and having different peak wavelengths are detected at single measurement, the wavelength regions of the two or more kinds of light partially overlap with each other in some cases. As a result, uniqueness of light detection decreases in some cases due to leakage into one kind of light to be detected from another kind of light not to be detected. The wavelength distribution and quantity of light are collectively referred to as a light wavelength distribution amount, and the wavelength distribution and light quantity of leakage light are collectively referred to as a light wavelength distribution amount not to be detected. The light receiving elements 100C to 100F cannot selectively receive an overlapping part of two or more light wavelength regions, and thus what is called fluorescence correction is performed to extract only optical information obtained from fluorescence to be detected by removing an electric signal attributable to fluorescence not to be detected from an electric signal of each of the light receiving elements 100C to 100F. Information on the light wavelength distribution amount not to be detected, which is included in the detected optical information is indicated as a fluorescence correction value in FIG. 4 and used for the fluorescence correction. The simplest fluorescence correction value is the light wavelength distribution amount of fluorescence not to be detected, which is to be subtracted from the light wavelength distribution amount of fluorescence to be detected. For example, two kinds of fluorescence having different peak wavelengths are referred to as fluorescence 1 and fluorescence 2. The fluorescence correction value of fluorescence 1 is 0.0 when light wavelength distribution does not overlap between fluorescence 1 and fluorescence 2 and no fluorescence correction is needed. When light distribution wavelength overlapping is observed at simultaneous measurement of fluorescence 1 and fluorescence 2 and the amount of the light wavelength distribution overlapping is 27.5%, the fluorescence correction value is set to be 27.5 to subtract 27.5% of a fluorescence distribution amount attributable to fluorescence 2 from the fluorescence distribution amount of fluorescence 1.

The gating related information includes information on distribution setting on a distribution diagram of the light attributable to particles. For one measurement item or each of two or more measurement items, the flow cytometer produces a distribution diagram such as a scattergram or a histogram of the light attributable to particles from detected optical information. The scattergram illustrates distribution of the light attributable to particles on the two axes of an X axis and a Y axis for two measurement items. The histogram illustrates the strength of light and the number of particles for one measurement item. Gating is selection of a certain distribution region in accordance with a measurement item in each distribution diagram to perform appropriate measurement in accordance with the measurement item. More specifically, the gating is setting of information described below.

The information on distribution setting on the distribution diagram of the light attributable to particles includes information on a scattergram, information on a histogram, and information on a gate. The information on a scattergram is information for producing a scattergram and includes a scattergram name as the name of the produced scattergram, a higher-level gate, an X-axis channel (also referred to as X-axis ch) indicating a photodiode receiving light representing a first measurement item, the name of the X-axis channel, a Y-axis channel (also referred to as Y-axis ch) indicating a photodiode receiving light representing a second measurement item, and the name of the Y-axis channel.

The information on a histogram is information for producing a histogram and includes a histogram name, a higher-level gate, an X-axis channel indicating a photodiode receiving light representing a measurement item, and the name of the X-axis channel. The higher-level gate is a gate of a scattergram produced first when two or more gates are used to produce scattergrams corresponding to the respective gates. The information on a gate is used to determine each particle region selected from a scattergram or a histogram and includes a gate name as the name of a selected gate, position information indicating the position of the gate, a color provided to the wavelength or wavelength region of received light on the display unit, a measurement item name, the upper limit value of the intensity of received light, the lower limit value of the intensity of received light, and a result value type when an analysis result is displayed. The result value type includes various statistically processed values of a result and is, for example, a particle total number, an average value, a variation coefficient, a ratio relative to the whole, or a mode value.

The number of produced scattergrams and histograms differs depending on each measurement item. Thus, a plurality of pieces of the information on a scattergram, a plurality of pieces of the information on a histogram, and a plurality of pieces of the information on a gate are included in accordance with the number of produced scattergrams and histograms in some cases. The information on distribution setting on the distribution diagram of the light attributable to particles may include information on a dot plot.

[Information Processing System of Flow Cytometer]

FIG. 5 is a diagram illustrating an exemplary information processing system of the flow cytometer according to one or more embodiments. FIG. 5 illustrates the configuration of the information processing system of the flow cytometer 10, which includes, as an example, an input unit 60, a condition input unit 61, the display unit 62, the signal processing unit 63, and the communication unit 64. The signal processing unit 63 acquires, through the amplification units 130A to 130F and the A/D conversion units 131A to 131F, the detection signals output from the light receiving elements 100A to 100F. The information processing system also includes the temperature sensor 22 that detects the temperature of the particle-containing liquid and outputs a temperature detection signal converted into an electric signal. The signal processing unit 63 acquires the temperature detection signal from the temperature sensor 22 through a temperature detection circuit 132 and an A/D conversion unit 133.

The input unit 60 is achieved by, for example, at least one of a keyboard, a mouse, and a touch panel, and receives inputting for changing a measurement item or the like from a user operating the flow cytometer 10.

The condition input unit 61 is achieved by, for example, at least one of a keyboard, a mouse, and a touch panel, and receives inputting of a measurement condition from the user operating the flow cytometer 10.

The display unit 62 is achieved by, for example, a monitor, and displays a measurement item, a measurement condition, a test result, or the like.

The input unit 60, the condition input unit 61, and the display unit 62 are disposed in the information processing device 14 connected with the flow cytometer body 13, but may be disposed in the flow cytometer body 13.

The communication unit 64 is achieved by, for example, a communication device used to communicate with the electronic medical record system 1 through the communication network N1 illustrated in FIG. 1.

As an example, the signal processing unit 63 includes a memory 82 used as a work area of data processing, a storage unit 83 in which a computer program and processing data are recorded, a central processing unit (CPU) 81 that performs data processing to be described later, and a bus 84 through which data is transmission between the components. As an example, the signal processing unit 63 also includes interface units (denoted by "I/F units" in FIGS. 5) 85 and 86 through which data inputting and outputting are performed with the units 60, 61, 62, and 64 connected with the signal processing unit 63, to which the detection signals output from the light receiving elements 100A to 100F are input through the amplification units 130A to 130F and the A/D conversion units 131A to 131F, and to which the temperature detection signal from the temperature sensor 22 is input through the temperature detection circuit 132 and the A/D conversion unit 133.

In the following description, unless otherwise stated, processing performed by the signal processing unit 63 means processing performed by the CPU 81 of the signal processing unit 63 in reality. The CPU 81 temporarily stores necessary data (such as intermediate data being processed) in the memory 82 as a work area, and records data to be stored for a long period in the storage unit 83 as appropriate.

Figure 6:
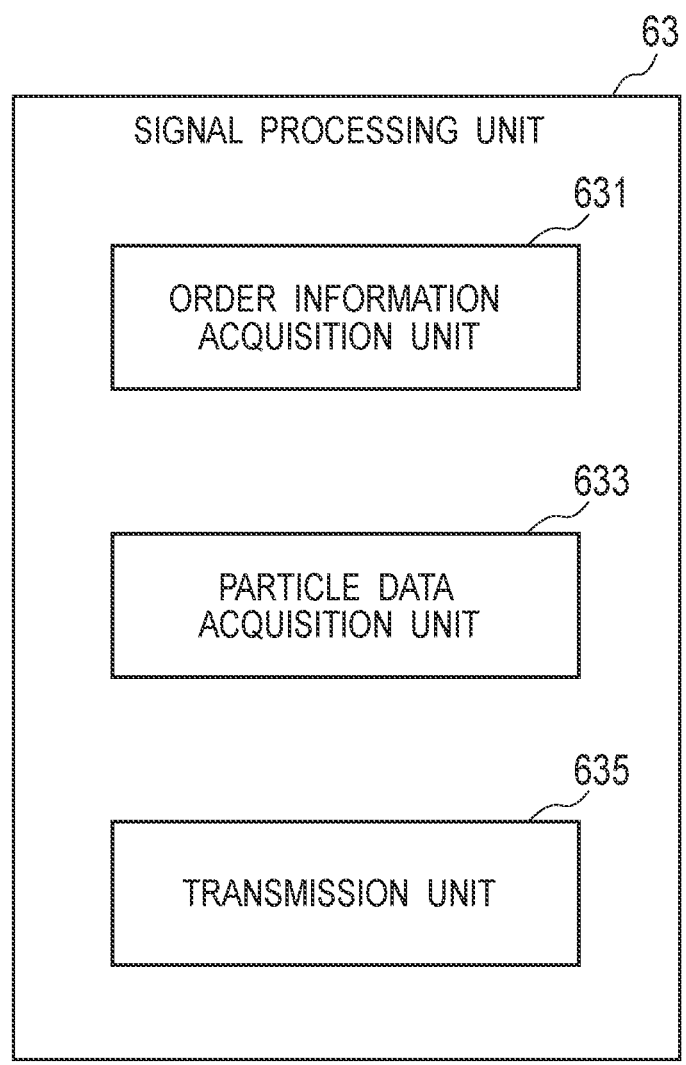
FIG. 6 is a diagram illustrating an exemplary functional block of an information processing unit according to one or more embodiments.

FIG. 6 is a diagram illustrating an exemplary functional block of an information processing unit according to one or more embodiments. As illustrated in FIG. 6, the signal processing unit 63 executes a computer program stored in the storage unit 83 or the memory 82 illustrated in FIG. 5 to achieve, as an example, an order information acquisition unit 631 that acquires order information including one or more measurement items, a particle data acquisition unit 633 that measure particles contained in a sample based on the measurement items to acquire particle data of the particles, and a transmission unit 635 that transmits at least one of the particle data and data on the particle distribution diagram of the particles generated based on the particle data to at least one of the HIS 2 and the LIS 4 illustrated in FIG. 1. As an example, the signal processing unit 63 may function as an order information acquisition unit 631 that acquires order information including one or more measurement items. The signal processing unit 63 controls operation of each component connected with the signal processing unit 63.

[Data Transmission Processing]

Figure 7:
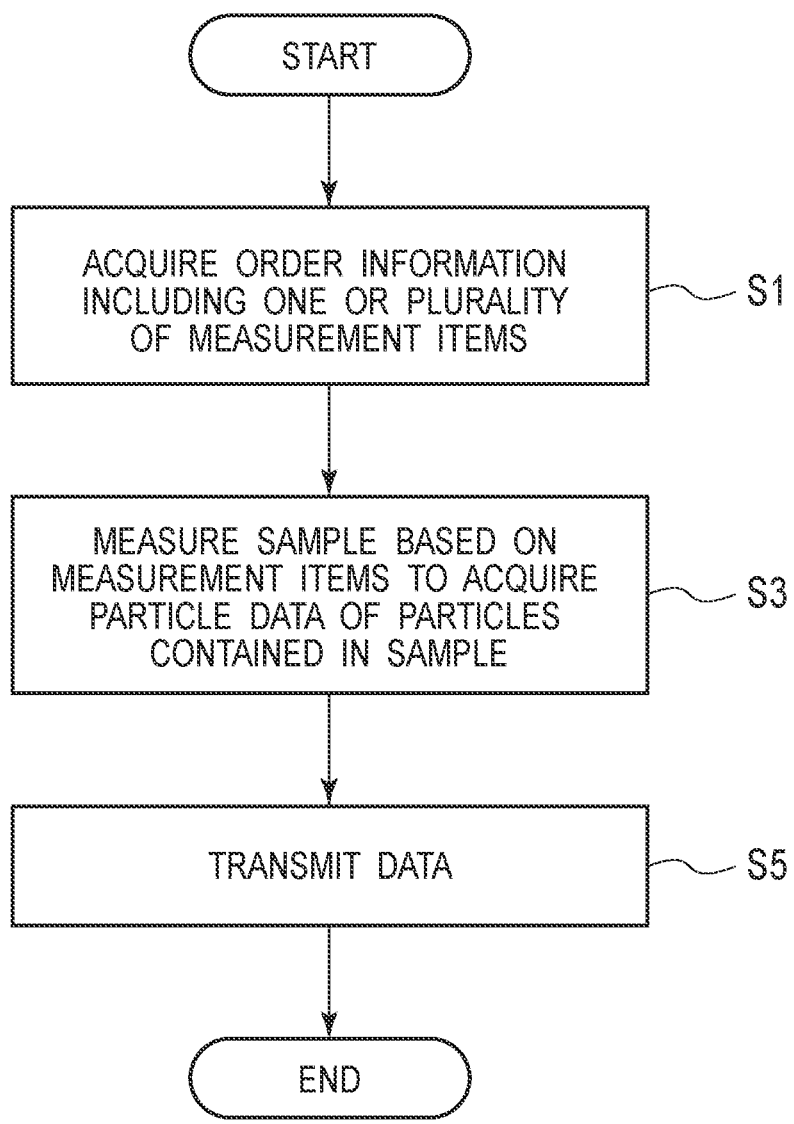
FIG. 7 is a diagram illustrating exemplary data transmission processing performed by a flow cytometer according to one or more embodiments.

FIG. 7 is a diagram illustrating exemplary data transmission processing performed by the flow cytometer according to one or more embodiments.

(Step S1)

The order information acquisition unit 631 of the signal processing unit 63 of the flow cytometer 10 illustrated in FIGS. 5 and 6 acquires order information including one or more measurement items from at least one of the HIS 2 and the LIS 4. Before being acquired by the flow cytometer 10 illustrated in FIG. 1, the order information may be acquired by a pretreatment device (not illustrated) that executes or performs pretreatment of preparing a measurement specimen from a sample. In this case, the pretreatment device prepares the measurement specimen from the sample in accordance with the measurement items included in the order information, and provides the prepared measurement specimen to the flow cytometer 10 together with information on the measurement items.

(Step S3)

The flow cytometer 10 measures particles contained in the sample based on the measurement items included in the order information acquired by the order information acquisition unit 631, thereby acquiring particle data of the particles. With this configuration, the particles contained in the sample can be measured in accordance with the one or more measurement items included in the order information, and thus a measurement result in accordance with each measurement item can be acquired.

After the pretreatment of preparing a measurement specimen from a sample is executed by the pretreatment device, the flow cytometer 10 may measure particles contained in the measurement specimen.

With this configuration, it is possible to perform particle measurement more suitable for a measurement item included in a measurement order by executing the pretreatment of preparing a measurement specimen from a sample, and thus accurate particle data can be acquired.

(Step S5)

The transmission unit 635 transmits at least one of particle data and data on the particle distribution diagram of the particles generated based on the particle data to at least one of the HIS 2 and the LIS 4 illustrated in FIG. 1. For example, the transmission unit 635 transmits, in a format compliant with a predetermined standard, at least one of particle data and data on the particle distribution diagram of the particles generated based on the particle data. With this configuration, data is transmitted in a format compliant with a predetermined standard, and thus can be reliably transmitted.

The predetermined standard is a standard compliant with Clinical and Laboratory Standards Institute (CLSI). CLSI is an international standard for standardization of general medical instruments. With this configuration, data is transmitted in a format compliant with CLSI as an international standard, and thus can be reliably transmitted.

The predetermined standard may include at least one of standards of American Society for Testing and Materials (ASTM), Health Level Seven (HL7), Integrating the Healthcare Enterprise (IHE), Digital Imaging and Communications in Medicine (DICOM), and Medical waveform Format Encoding Rules (MFER). With this configuration, it is possible to use various standards related to information communication, and thus the range of selection related to the format of data transmission is increased.

As described above, the predetermined standard may include various standards, but the following description will be made with an ASTM protocol in detail.

Figure 8:
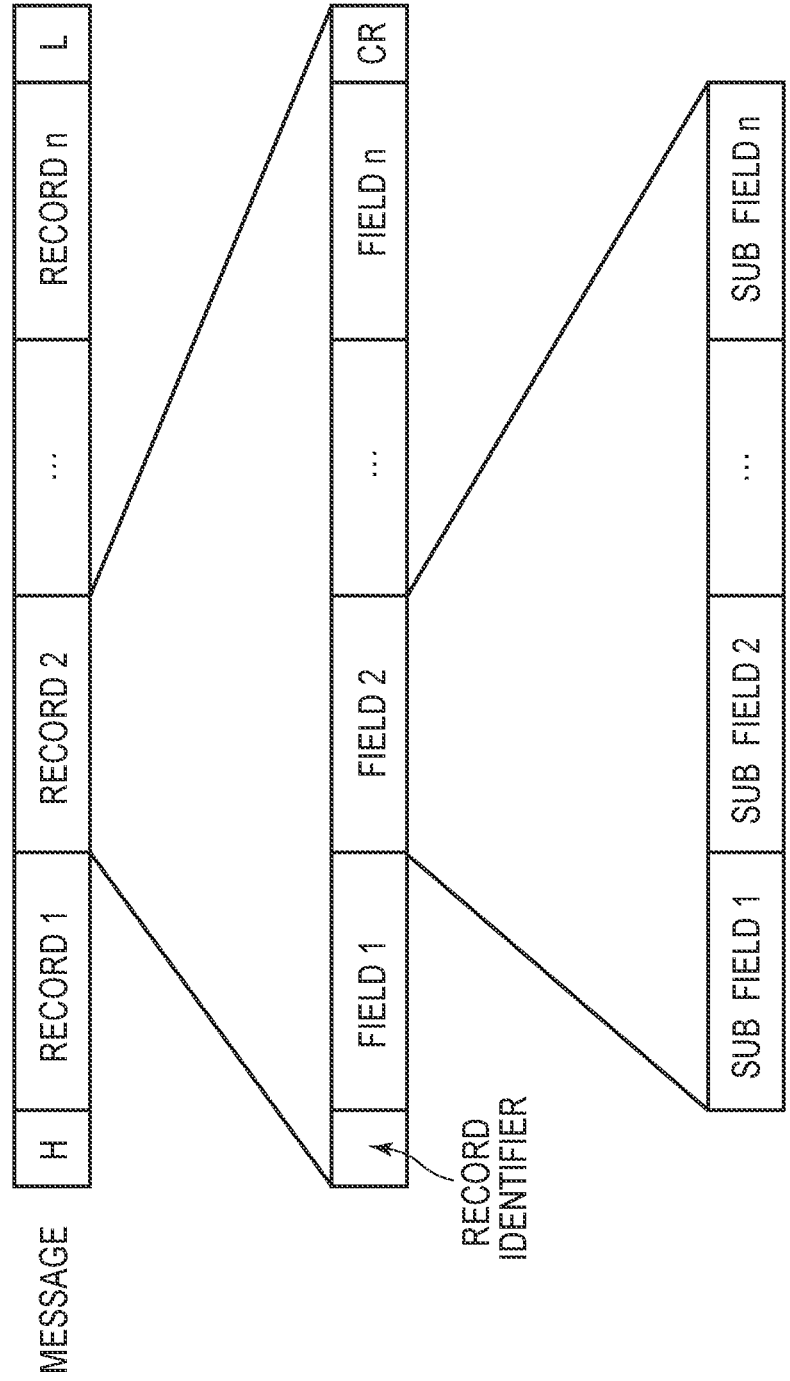
FIG. 8 is a diagram illustrating an exemplary format of data transmitted from a flow cytometer according to one or more embodiments.

FIG. 8 is a diagram illustrating an exemplary format of data transmitted from the flow cytometer according to one or more embodiments. FIG. 8 illustrates an exemplary ASTM protocol, and as an example, each data is disposed and transmitted at four components of an ASTM message, a record, a field, and a sub field. First, data is transmitted by using "message". The "message" includes columns of "record", starts with a message header record (H), and ends with a message stop record (L). Each "record" includes columns of "field", and includes a series of characters starting with an ASCII alphabet called a record identifier and ending with [CR]. Each "field" includes columns of "sub field".

FIG. 9 is a diagram illustrating an exemplary configuration of an ASTM record illustrated in FIG. 8. As illustrated in FIG. 9, each record type is identified through allocation of a record identifier. For example, "message" including a "measurement result" record (first record) corresponding to Record Identifier R is transmitted including a "patient information" record (second record) corresponding to Record Identifier P. Thus, the transmission unit 635 illustrated in FIG. 6 may transmit, for each sample, a message including patient information associated with the sample and at least one (measurement result) of particle data and data on the particle distribution diagram of particles generated based on the particle data.

With this configuration, for each sample, a result of measurement of particles contained in the sample is transmitted in association with patient information, and thus it is possible to accurately output an electronic medical record of a patient that a doctor desires to browse at the electronic medical record system 1 illustrated in FIG. 1.

"Message" including a "measurement result" record corresponding to Record Identifier R may be transmitted further including a "measurement request" record corresponding to Record Identifier O in addition to a "patient information" record corresponding to Record Identifier P.

FIG. 10 is a diagram illustrating an exemplary configuration of ASTM field 8 illustrated in FIG. 8. As illustrated in FIG. 10, patient information includes at least patient identification information (ASTM field 8.1.5) that identifies a patient. With this configuration, a sample associated with a particular patient can be more accurately identified in the electronic medical record system 1 illustrated in FIG. 1.

FIG. 11 is a diagram illustrating an exemplary configuration of ASTM field 10 illustrated in FIG. 8. As illustrated in FIG. 11, at least one of particle data and data on the particle distribution diagram of particles is disposed in "data value" of ASTM field 10.1.4 and transmitted to the electronic medical record system 1 illustrated in FIG. 1.

FIG. 12 is a diagram illustrating an exemplary communication data format of dot data included and transmitted in "data value" of ASTM field 10.1.4 illustrated in FIG. 11. As illustrated in FIG. 12, the dot data is included and transmitted in "data value" of ASTM field 10.1.4. Then, having acquired the dot data (output information) from the flow cytometer 10, the electronic medical record system 1 illustrated in FIG. 1 generates, based on the acquired dot data, an electronic medical record including a dot plot (particle distribution diagram) corresponding to the dot data, and outputs the electronic medical record. The dot data is data corresponding to each particle measured by the flow cytometer 10, in other words, data for each dot of the particle.

FIG. 13 is a diagram illustrating an exemplary communication data format of granularity distribution data included and transmitted in "data value" of ASTM field 10.1.4 illustrated in FIG. 11. As illustrated in FIG. 12, the granularity distribution data is included and transmitted in "data value" of ASTM field 10.1.4. Then, when having acquired the granularity distribution data (output information) from the flow cytometer 10, the electronic medical record system 1 illustrated in FIG. 1 generates and outputs an electronic medical record including a histogram (particle distribution diagram) corresponding to the granularity distribution data based on the acquired granularity distribution data. The granularity distribution data is data indicating the distribution status of particles measured by the flow cytometer 10.

With this configuration, image data corresponding to the particle distribution diagram does not need to be transmitted, and thus it is possible to reduce the amount of transmitted data.

The output information includes output information for use to output a plurality of different particle distribution diagrams based on acquired particle data. With this configuration, for example, it is possible to display, in comparison, particle distribution diagrams corresponding to particle data measured for a sample on different dates and times.

The output information further includes date and time information indicating date and time at which particles contained in the sample are measured, or the date and time of the measurement of the particles in the sample. With this configuration, for example, it is possible to display, in a temporal sequence, particle distribution diagrams corresponding to particle data for the sample.

The transmission unit 635 illustrated in FIG. 6 may transmit image data illustrating a particle distribution diagram to the electronic medical record system 1 illustrated in FIG. 1. As an example, the transmission unit 635 may transmit, to the electronic medical record system 1, particle data including forward scattered light information indicating the size of a cell (particle), side scattered light information indicating the internal structure of the cell, and fluorescence information for knowing information of protein, gene, or the like in the cell.

Figure 14:
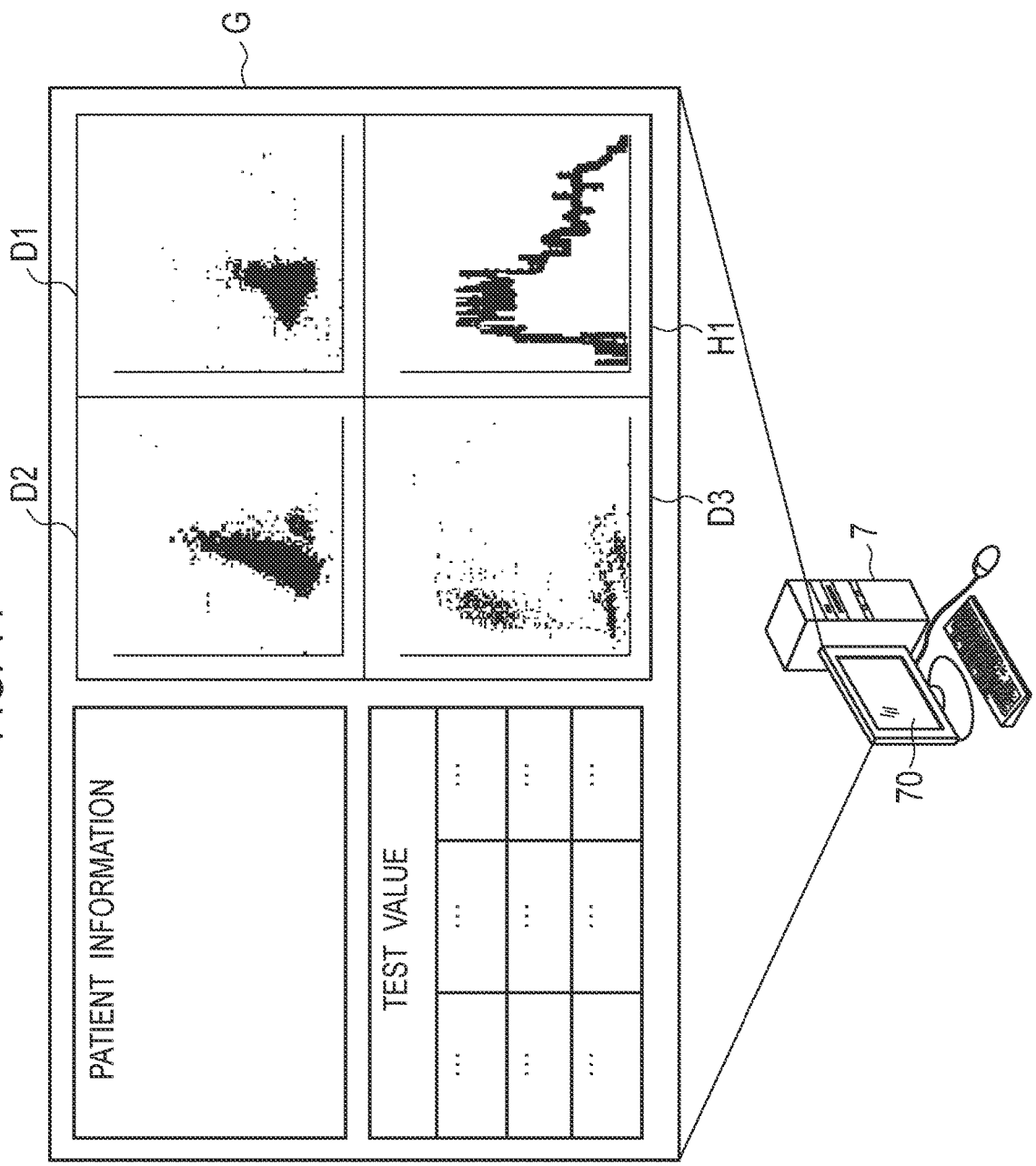
FIG. 14 is a diagram illustrating an exemplary electronic medical record display screen on a display unit of a doctor terminal device according to one or more embodiments.

FIG. 14 is a diagram illustrating an exemplary electronic medical record display screen on a display unit of the doctor terminal device according to one or more embodiments. As illustrated in FIG. 14, an electronic medical record including patient information, the test value of a sample associated with a patient, dot plots D1, D2, and D3 (particle distribution diagrams) corresponding to the dot data illustrated in FIG. 12, and a histogram H1 (particle distribution diagram) corresponding to the granularity distribution data illustrated in FIG. 13 is output on an electronic medical record display screen G on a display unit 70 of the doctor terminal device 7.

With this configuration, data of particles contained in a sample is displayed in at least one of a dot plot and a histogram, and thus it is possible to appropriately understand the distribution state of the particles.

In addition, since the particle distribution diagrams are displayed in a list in association with the patient information and the test value of a sample associated with a patient, it is possible to easily understand test results of the patient.

As described above, according to one or more embodiments, the flow cytometer 10 transmits at least one of particle data of particles contained in a sample and data on a particle distribution diagram of the particles generated based on the particle data to the electronic medical record system 1. With this configuration, an electronic medical record including the particle distribution diagram of the particles contained in the sample can be generated in the electronic medical record system 1 and browsed at, for example, the doctor terminal device 7 or the laboratory technician terminal device 9 of the electronic medical record system 1. In addition, the particle distribution diagram in the electronic medical record can be adjusted as necessary. Thus, it is possible to increase the operability of the electronic medical record system 1 and improve convenience when the electronic medical record is browsed, and in addition, accurate diagnosis can be performed quickly by a doctor or the like.

Other Embodiments

The above-described embodiments are intended to facilitate understanding of the present invention and should not be understood to limit the present invention. One or more embodiments may be changed and modified (for example, embodiments may be combined, or part of the configuration of each embodiment may be omitted) without departing from the scope of the invention. In addition, one or more embodiments include equivalents thereof.

The transmission unit 635 of the signal processing unit 63 of the flow cytometer illustrated in FIG. 6 may transmit at least one of particle data and data on a particle distribution diagram to the HIS 2 through the LIS 4 illustrated in FIG. 1.

With this configuration, data can be transmitted through the LIS 4 when the flow cytometer 10 is not directly connected with the HIS 2.

The transmission unit 635 may transmit compressed data including at least one of particle data and data on the particle distribution diagram of particles, which is generated based on the particle data, to at least one of the hospital information system 2 and the clinical laboratory information system 4.

With this configuration, transmission data to at least one of the HIS 2 and the LIS 4 is compressed, and thus it is possible to reduce the amount of transmitted data.

The transmission unit 635 may further transmit particle number information on the number of particles.

With this configuration, since the transmission unit 635 further transmits the particle number information on the number of particles, it is possible to generate and output an electronic medical record further including the number of particles as a test value in the electronic medical record system 1 illustrated in FIG. 1.

The invention claimed is:

1. A flow cytometer for measuring particles in a sample treated with plural kinds of labeling antibody pigments to acquire particle data comprising plural kinds of optical information of the particles, respective ones of the plural kinds of optical information being attributable to respective ones of the plural kinds of labeling antibody pigments, the flow cytometer comprising:
   a flow cell,
   light sources configured to emit light to the particles in the sample passing through the flow cell;
   light receiving elements including first and second light receiving elements, the first light receiving element receiving first fluorescence from the particles in the sample that are labeled with a first fluorescent labeling antibody pigment and the second light receiving element receiving second fluorescence from the particles in the sample that are labeled with a second fluorescent labeling antibody pigment;
   a processor configured with a program to perform operations comprising:
   receiving order information comprising a measurement item and a measurement condition associated with the measurement item, the measurement condition of the measurement item comprising: (1) adjustment information on adjustment of detection sensitivity for detecting the plural kinds of optical information; (2) correction information on correction of the plural kinds of optical information to extract the first fluorescence from a first detection signal detected by the first light receiving element and to extract the second fluorescence from a second detection signal detected by the second light receiving element; and (3) gating information comprising a selection of one or more distribution regions in accordance with the measurement item in each of one or more particle distribution diagrams;
   measuring according to the measurement condition of the measurement item, the particles in the sample treated with the plural kinds of labeling antibody pigments to acquire particle data comprising the plural kinds of optical information of the particles, the measuring comprising:
   adjusting the detection sensitivity based on the adjustment information;
   extracting the first fluorescence from the first detection signal detected by the first light receiving element and extracting the second fluorescence from the second detection signal detected by the second light receiving element based on the correction information; and
   selecting one or more distribution regions in accordance with the measurement item in each of one or more particle distribution diagrams based on the gating information;
   generating at least one of: particle distribution diagram output information comprising one or more dot plots of the particles based on the particle data; and image data representing one or more dot plots of the particles based on the particle data; and
   transmitting at least one of the particle data, the particle distribution diagram output information, and the image data, to at least one of a hospital information system that supports hospital operations and a clinical laboratory information system that supports clinical test operations.

2. The flow cytometer according to claim 1, wherein receiving the order information comprises receiving the order information from the at least one of the hospital information system and the clinical laboratory information system.

3. The flow cytometer according to claim 1, wherein the the one or more dot plots comprises a plurality of dot plots different from each other.

4. The flow cytometer according to claim 1, wherein the particle distribution diagram output information further comprises date and time information comprising date and time of the measurement of the particles in the sample.

5. The flow cytometer according to claim 1, wherein the optical information further comprises scattered light information of the particles.

6. The flow cytometer according to claim 1, wherein the at least one of the particle data, the particle distribution diagram output information, and the image data is transmitted in a format compliant with a predetermined standard.

7. The flow cytometer according to claim 1, wherein the processor is configured with the program to perform operations further comprising transmitting patient information associated with the sample to the at least one of the hospital information system and the clinical laboratory information system.

8. The flow cytometer according to claim 7, wherein the patient information comprises patient identification information that identifies a patient.

9. The flow cytometer according to claim 1, wherein the processor is configured with the program to perform operations further comprising transmitting a message to the at least one of the hospital information system and the clinical laboratory information system, and the message comprises:
   patient information associated with the sample; and
   the at least one of the particle data, the particle distribution diagram output information, and the image data.

10. The flow cytometer according to claim 9, wherein the message comprises:
   a first record comprising the at least one of the particle data, the particle distribution diagram output information, and the image data; and
   a second record comprising the patient information.

11. The flow cytometer according to claim 1, wherein the processor is configured with the program to perform operations such that transmitting the at least one of the particle data, the particle distribution diagram output information, and the image data comprises transmitting the at least one of the particle data, the particle distribution diagram output information, and the image data to the hospital information system through the clinical laboratory information system.

12. The flow cytometer according to claim 1, wherein the particle distribution diagram output information comprises the one or more dot plots and a histogram.

13. The flow cytometer according to claim 1, wherein the processor is configured with the program to perform operations such that transmitting the at least one of the particle data, the particle distribution diagram output information, and the image data comprises transmitting compressed data comprising the at least one of the particle data, the particle distribution diagram output information, and the image data to the at least one of the hospital information system and the clinical laboratory information system.

14. The flow cytometer according to claim 1, wherein the processor is configured with the program to perform operations further comprising transmitting particle number information on the number of the particles.

15. The flow cytometer according to claim 1, wherein
the correction information of the optical information included in the measurement condition includes (2a) a correction value of the second fluorescence that is detected by the first light receiving element and is to be removed from the first detection signal detected by the first light receiving element and (2b) a correction value of the first fluorescence that is detected by the second light receiving element and is to be removed from the second detection signal detected by the second light receiving element.

16. A method to be executed by a computer for measuring particles in a sample treated with plural kinds of labeling antibody pigments to acquire particle data comprising plural kinds of optical information of the particles, respective ones of the plural kinds of optical information being attributable to respective ones of the plural kinds of labeling antibody pigments, wherein the plural kinds of optical information of the particles includes a first fluorescence, received by a first light receiving element, from the particles that are labeled with a first fluorescent labeling antibody pigment and a second fluorescence, received by a second light receiving element, from the particles that are labeled with a second fluorescent labeling antibody pigment, the method comprising:
receiving order information comprising a measurement item and a measurement condition associated with the measurement item, the measurement condition of the measurement item comprising: (1) adjustment information on adjustment of detection sensitivity for detecting the plural kinds of optical information; (2) correction information on correction of the plural kinds of optical information to extract the first fluorescence from a first detection signal from the first light receiving element and to extract the second fluorescence from a second detection signal from the second light receiving element; and (3) gating information comprising a selection of one or more distribution regions in accordance with the measurement item in each of one or more particle distribution diagrams;
measuring according to the measurement condition of the measurement item, the particles in the sample treated with the plural kinds of labeling antibody pigments to acquire the particle data comprising the plural kinds of optical information of the particles, the measuring comprising:
adjusting the detection sensitivity based on the adjustment information;
extracting the first fluorescence from the first detection signal detected by the first light receiving element and extracting the second fluorescence from the second detection signal detected by the second light receiving element based on the correction information; and
selecting one or more distribution regions in accordance with the measurement item in each of one or more particle distribution diagrams based on the gating information;
generating at least one of particle distribution diagram output information comprising one or more dot plots of the particles based on the particle data and image data representing the one or more dot plots of the particles based on the particle data; and
transmitting at least one of the particle data, the particle distribution diagram output information, and the image data, to at least one of a hospital information system that supports hospital operations and a clinical laboratory information system that supports clinical test operations.

17. The method according to claim 16, wherein
the correction information of the optical information included in the measurement condition includes (2a) a correction value of the second fluorescence that is detected by the first light receiving element and is to be removed from the first detection signal detected by the first light receiving element and (2b) a correction value of the first fluorescence that is detected by the second light receiving element and is to be removed from the second detection signal detected by the second light receiving element.

* * * * *